United States Patent
Sato et al.

(10) Patent No.: US 9,165,386 B2
(45) Date of Patent: Oct. 20, 2015

(54) MAGNETIC RESONANCE IMAGING DEVICE, AND METHOD FOR GENERATING MAGNETIC SUSCEPTIBILITY ENHANCED IMAGE

(71) Applicant: Hitachi, Ltd., Tokyo (JP)

(72) Inventors: Ryota Sato, Tokyo (JP); Toru Shirai, Tokyo (JP); Yo Taniguchi, Tokyo (JP); Yoshihisa Soutome, Tokyo (JP); Yoshitaka Bito, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 14/342,186

(22) PCT Filed: Oct. 3, 2012

(86) PCT No.: PCT/JP2012/075698
§ 371 (c)(1),
(2) Date: Feb. 28, 2014

(87) PCT Pub. No.: WO2013/054718
PCT Pub. Date: Apr. 18, 2013

(65) Prior Publication Data
US 2014/0219533 A1 Aug. 7, 2014

(30) Foreign Application Priority Data
Oct. 12, 2011 (JP) ................. 2011-225244

(51) Int. Cl.
*G06K 9/00* (2006.01)
*G06T 11/00* (2006.01)
(Continued)

(52) U.S. Cl.
CPC ............... *G06T 11/008* (2013.01); *A61B 5/055* (2013.01); *G01R 33/5608* (2013.01); *G06T 5/001* (2013.01); *G01R 33/24* (2013.01); *G01R 33/5613* (2013.01); *G01R 33/5635* (2013.01);
(Continued)

(58) Field of Classification Search
None
See application file for complete search history.

(56) References Cited

U.S. PATENT DOCUMENTS 6,658,280 B1  12/2003  Haacke
7,782,051 B2  8/2010  Haacke et al.
(Continued)

FOREIGN PATENT DOCUMENTS

JP  2008-93418 A  4/2008

OTHER PUBLICATIONS

International Search Report from International Application No. PCT/JP12/075698 mailed Dec. 25, 2012.
(Continued)

*Primary Examiner* — Siamak Harandi
(74) *Attorney, Agent, or Firm* — Brundidge & Stanger, P.C.

(57) ABSTRACT

There is provided a technique for obtaining a magnetic susceptibility-weighted image in which contrast difference of a tissue of interest and a surrounding tissue can be emphasized regardless of the positional relationship of the $B_0$ direction and the imaging slice. A phase image is converted into a susceptibility map not depending on the $B_0$ direction, and then a weighting image used for weighting is generated by using the susceptibility map. The weighting image to be generated is for emphasizing contrast of a tissue of interest and a surrounding tissue depending on the purpose. Then, by multiplication of the weighting image and an absolute image, a magnetic susceptibility-weighted image in which the magnetic susceptibility difference is emphasized depending on the purpose is obtained.

9 Claims, 19 Drawing Sheets

(51) Int. Cl.
  *A61B 5/055* (2006.01)
  *G01R 33/56* (2006.01)
  *G06T 5/00* (2006.01)
  *G01R 33/561* (2006.01)
  *G01R 33/563* (2006.01)
  *G01R 33/24* (2006.01)
  *G01R 33/565* (2006.01)

(52) U.S. Cl.
  CPC . *G01R 33/56536* (2013.01); *G06T 2207/10088* (2013.01); *G06T 2207/30016* (2013.01)

(56) References Cited

U.S. PATENT DOCUMENTS

| | | | |
|---|---|---|---|
| 8,422,756 B2 | 4/2013 | Haacke et al. | |
| 2008/0071167 A1 | 3/2008 | Ikedo et al. | |
| 2009/0261824 A1 | 10/2009 | Haacke et al. | |
| 2011/0304330 A1* | 12/2011 | Yoneda et al. | 324/309 |

OTHER PUBLICATIONS

Deistung, et al., "Calculation of the Magnetic Susceptibility from Susceptibility Weighted Phase Images", Proc. Intl. Soc. Mag. Reson. Med. 17 (2009), p. 2931.

Haacke, et al., "Susceptibility Weighted Imaging and Susceptibility Mapping (SWIM): A New Means to Visualize Veins and Quantify Susceptibility" Proc. Intl. Soc. Mag. Reson. Med. 18, 2010, #5122.

Santiesteban et al., Object Orientation Independence of Susceptibility Weighted Imaging by Using a Sigmoid-Type Phase Window, Proc. Intl. Soc. Mag. Reson. Med. 14, 2006, #2399.

Neelavalli, et al., A Fast and Robust Method for Quantifying Magnetic Susceptibility of Arbitrarily Shaped Objects using MR, Proc. Intl. Soc. Mag. Reson. Med. 16, 2008, #3056.

International Preliminary Report on Patentability from International Application No. PCT/JP2012/75698 mailed on Aug. 14, 2014.

* cited by examiner

101

102

103

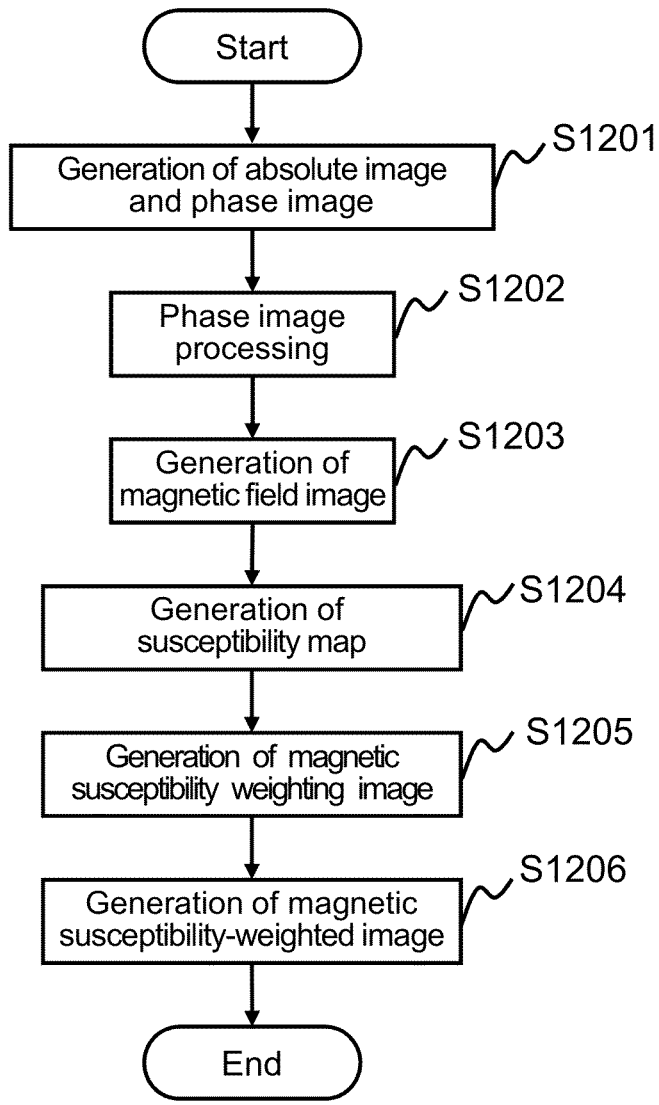

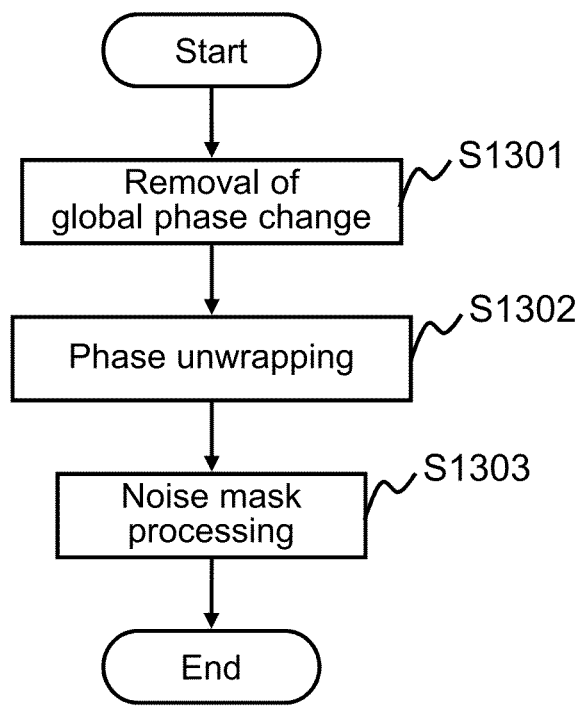

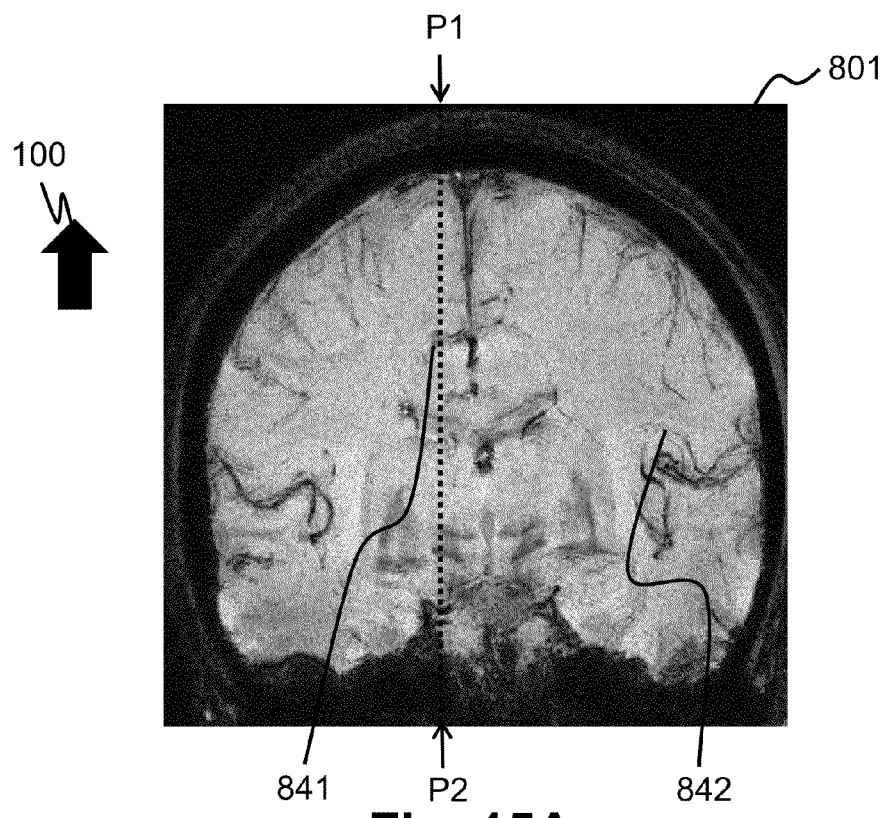
Fig. 15A
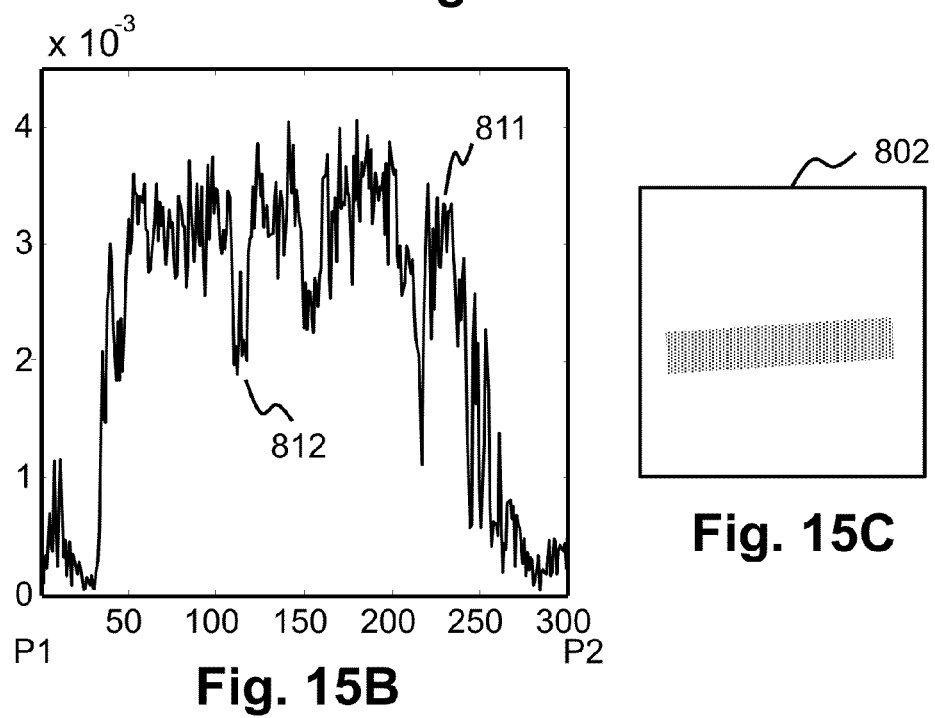
Fig. 15B
Fig. 15C

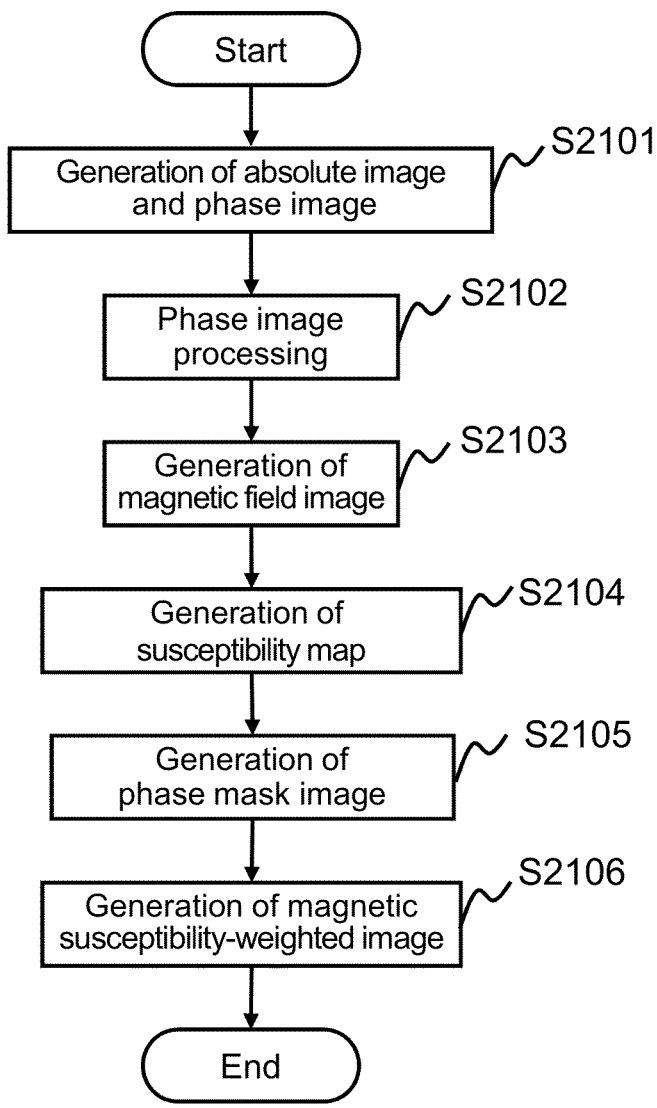

MAGNETIC RESONANCE IMAGING DEVICE, AND METHOD FOR GENERATING MAGNETIC SUSCEPTIBILITY ENHANCED IMAGE

TECHNICAL FIELD

The present invention relates to a magnetic resonance imaging (MRI) technique, especially, a technique for image processing of reconstructed images.

BACKGROUND ART

Magnetic resonance imaging (MRI) apparatuses are diagnostic imaging apparatuses for medical use, which apply a radio frequency magnetic field and a gradient magnetic field to a subject placed in a static magnetic field, measure signals generated from the subject by nuclear magnetic resonance, and form an image from the signals. There are mainly two kinds of MRI apparatuses, i.e., tunnel type apparatuses utilizing a horizontal magnetic field and open type apparatuses utilizing a vertical magnetic field, those of the former type apply a static magnetic field in the direction parallel to the body axis of the subject, and those of the latter type apply a static magnetic field in the direction perpendicular to the body axis of the subject.

With the MRI apparatuses, images can be obtained for arbitrary imaging planes. The imaging planes include those of the three kinds of sections perpendicular to one another, i.e., axial sections dividing the body into a head side and a leg side, coronal sections dividing the body into a belly side and a dorsal side, and sagittal sections dividing the body into a right side and a left side, as well as oblique sections obliquely dividing the body at arbitrary angles.

In MRI apparatuses, in general, a slice gradient magnetic field for specifying an imaging plane, and an excitation pulse for exciting magnetization in the plane (radio frequency magnetic field pulse) are simultaneously applied, and magnetic resonance signals (echoes) generated at the time of convergence of the excited magnetization are obtained. In the above process, in order to impart positional information to the magnetization, a phase encoding gradient magnetic field and a read-out gradient magnetic field perpendicular to each other on the imaging plane are applied during the period from the excitation to acquisition of the signals. The measured echoes are arranged in the k-space having a kx horizontal axis and a ky vertical axis, and subjected to inverse Fourier transform to perform image reconstruction.

Each of the pixel values of the reconstructed image is a complex number consisting of an absolute value and a declination (phase). These absolute value and phase are determined depending on the static magnetic field intensity, direction of the static magnetic field ($B_0$ direction), imaging parameters such as type of imaging sequence, pixel size, and repetition time, magnetization density in the subject, relaxation time (T1, T2), and so forth.

For usual diagnoses, gray-scale images of which pixel values are absolute values (absolute images) are used. The absolute images are advantageous for depiction of tissue structures, and include various kinds of images, such as proton (hydrogen nucleus) density-weighted images, T1-weighted images, T2-weighted images, diffusion-weighted image, and vascular images. On the other hand, gray-scale images of which pixel values are phase values (phase images) are images reflecting spatial distribution of magnetic field intensity. The phase images are frequently used for adjustment of measurement parameters or the like, but are not used for diagnosis so frequently.

However, the SWI (susceptibility-weighted imaging) method based on the fact that the phase images reflect difference of magnetic susceptibility between tissues has been developed in recent years, and actively utilized (refer to, for example, Patent document 1). The SWI method is a technique for image processing, and in this method, weighting is performed for an absolute image by using a phase image. In the images obtained through the image processing according to the SWI method, there are imaged veins, small hemorrhagic lesions, siderotic tissues, and so forth, containing a lot of paramagnetic substances and showing a higher magnetic susceptibility value compared with surrounding tissue.

In the SWI method, a phase mask image as a weighting image in which signal intensities of negative phase regions are reduced is formed first by using a phase image, and an absolute image is multiplied by this phase mask image to form an image in which the negative phase regions are emphasized in black (magnetic susceptibility-weighted image). Further, when the magnetic susceptibility-weighted images are displayed, the minimum intensity projection (minIP) processing is performed for a plurality of continuous magnetic susceptibility-weighted images. The minIP processing is one of the methods for projecting a plurality of images in one image. In the projected image, the minimum pixel value among the corresponding pixel values of the plurality of image to be projected is set as the pixel value for every pixel.

The contrast of the phase images reflects local change of magnetic field caused by the magnetic susceptibility difference between tissues and changes depending on the $B_0$ direction. Therefore, the contrast of the magnetic susceptibility-weighted images generated by the SWI method, which uses a phase image for creation of the weighted images, also changes depending on the $B_0$ direction. For example, it is known that the magnetic susceptibility-weighted images created by the SWI method suffer from a $B_0$ direction dependency, for example, veins in an imaging slice substantially perpendicular to the $B_0$ direction can be emphasized, whereas imaging ability for veins of the other imaging slices, especially an imaging slice parallel to the $B_0$ direction, is reduced (refer to, for example, Patent document 2).

PRIOR ART REFERENCES

Patent Documents

Patent document 1: U.S. Pat. No. 6,658,280
Patent document 2: Japanese Patent Unexamined Publication (KOKAI) No. 2008-93418

DISCLOSURE OF THE INVENTION

Object to be Achieved by the Invention

Since the SWI method suffers from the $B_0$ direction dependency, it cannot emphasize contrast difference of a tissue of interest, such as veins, and surrounding tissues in the magnetic susceptibility-weighted images of an imaging slice not perpendicular to the $B_0$ direction, such as coronal section and sagittal section images obtained by horizontal magnetic field MRI apparatuses, and axial section and sagittal section images obtained by vertical magnetic field MRI apparatuses, and therefore the diagnostic ability is degraded. Therefore, when it is attempted to obtain highly diagnostically useful images, the imaging slice is limited depending on the $B_0$ direction of the MRI apparatus to be used.

The present invention was accomplished in light of the aforementioned circumstances, and an object of the present invention is to provide a technique for obtaining a magnetic susceptibility-weighted image in which contrast difference of a tissue of interest and surrounding tissues thereof can be emphasized regardless of the positional relationship of the $B_0$ direction and the imaging slice.

Means for Achieving the Object

According to the present invention, a phase image is converted into a susceptibility map, which is not depending on the $B_0$ direction, and then a weighting image used for weighting is generated by using the susceptibility map. In the generated weighting image, contrast difference of a tissue of interest and surrounding tissues is emphasized depending on the purpose. Further, by multiplication of an absolute image and the weighting image, a magnetic susceptibility-weighted image in which magnetic susceptibility difference is emphasized depending on the purpose is obtained.

Specifically, there is provided a magnetic resonance imaging apparatus comprising a measurement part for applying a radio frequency magnetic field and a gradient magnetic field to a subject placed in a static magnetic field and detecting magnetic resonance signals generated from the subject as complex signals, an operation part for performing an operation for the complex signals to generate an image, and a display processing part for displaying the generated image on a display device, wherein the operation part comprises an image reconstruction part for reconstructing a complex image in which pixel values are complex numbers from the complex signals, and an image conversion part for converting the complex image into a magnetic susceptibility-weighted image, and the image conversion part comprises a complex image conversion part for generating an absolute image and a phase image from absolute value components and phase components of the complex numbers of pixels of the complex image, respectively, a magnetic field image generation part for generating a magnetic field image representing spatial distribution of magnetic field intensity from the phase image, a susceptibility map generation part for generating a susceptibility map from the magnetic field image, a weighting image generation part for generating a weighting image for performing weighting for enhancing contrast difference of a tissue of interest and a surrounding tissue from the susceptibility map, and a magnetic susceptibility-weighted image generation part for generating a magnetic susceptibility-weighted image by multiplication of the absolute image and the weighting image.

Further, there is also provided a magnetic susceptibility-weighted image generation method for generating, from a complex image of which pixel values are complex numbers, a magnetic susceptibility-weighted image in which magnetic susceptibility difference calculated from the complex image is emphasized, which comprises a complex image conversion step of generating an absolute image and a phase image from absolute value components and phase components of complex numbers of pixels of the complex image, respectively, a magnetic field image generation step of generating a magnetic field image representing spatial distribution of magnetic field intensity from the phase image, a susceptibility map generation step of generating a susceptibility map from the magnetic field image, a weighting image generation step of generating a weighting image for performing weighting for emphasizing contrast difference of a tissue of interest and a surrounding tissue from the susceptibility map, and a magnetic susceptibility-weighted image generation step of generating a magnetic susceptibility-weighted image by multiplication of the absolute image and the weighting image.

Effect of the Invention

According to the present invention, a magnetic susceptibility-weighted image in which contrast difference of a tissue of interest and surrounding tissues can be emphasized can be obtained regardless of the positional relationship between the $B_0$ direction and the imaging slice.

BRIEF DESCRIPTION OF THE DRAWINGS

FIG. 8 is a flowchart of the image conversion process according to the first embodiment.

FIG. 9 is a flowchart of the phase image processing according to the first embodiment.

FIG. 15A is an explanatory drawing for explaining an example of magnetic susceptibility-weighted image formed by the SWI method.

FIG. 15B is an explanatory drawing for explaining the luminance profile of the magnetic susceptibility-weighted image shown in FIG. 15A.

FIG. 15C is an explanatory drawing for explaining the vein imaging ability in the magnetic susceptibility-weighted image formed by the SWI method.

FIG. 19 is a flowchart of the image conversion processing according to the second embodiment.

MODES FOR CARRYING OUT THE INVENTION

Hereafter, embodiments of the present invention will be explained with reference to the drawings. In all the drawings for explaining the embodiments, components having the same functions are indicated with the same numerals, unless specifically mentioned, and repetitive explanations thereof are omitted. The present invention is no way limited by the following descriptions.

First Embodiment

Figure 1A:
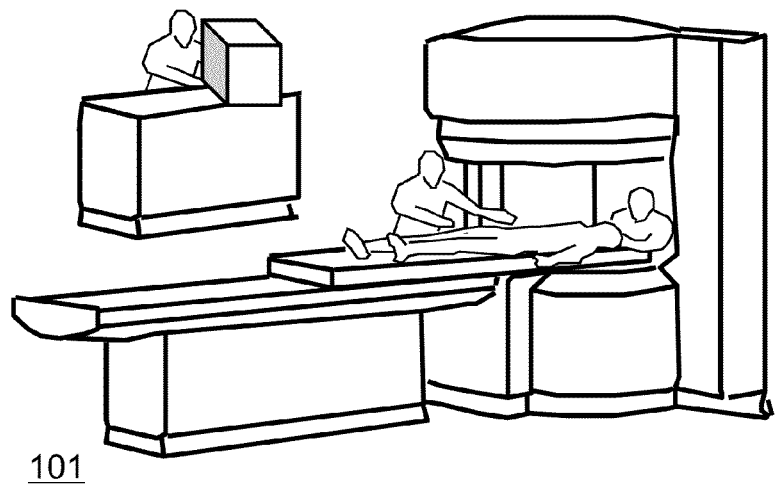
FIG. 1A is an external view of a magnetic resonance imaging apparatus of the vertical magnetic field type.
Figure 1B:
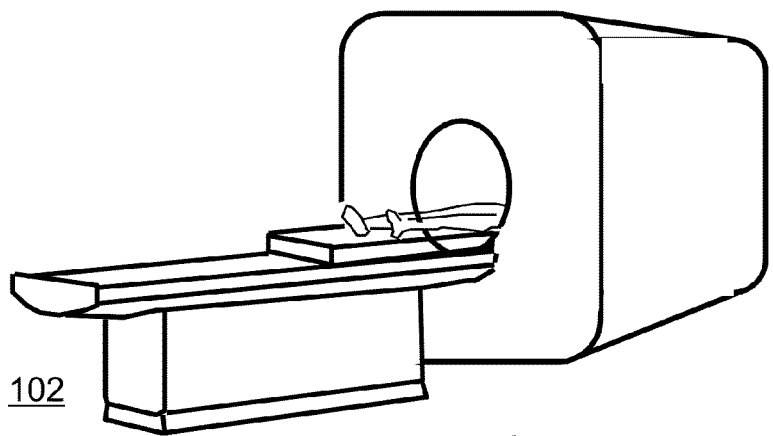
FIG. 1B is an external view of a magnetic resonance imaging apparatus of the horizontal magnetic field type.
Figure 1C:
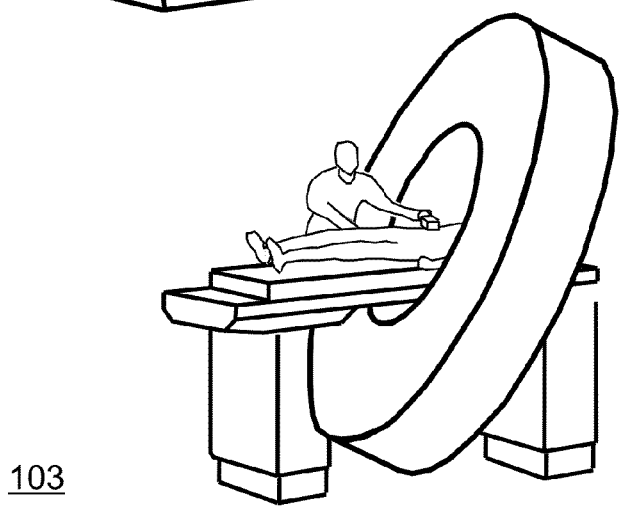
FIG. 1C is an external view of a magnetic resonance imaging apparatus in which spaciousness is improved.

The first embodiment of the present invention will be explained below. First, magnetic resonance imaging apparatuses (MRI apparatuses) according to this embodiment will be explained. FIGS. 1A to 1C are external views of MRI apparatuses according to this embodiment. FIG. 1A shows an MRI apparatus 101 of the vertical magnetic field type (vertical magnetic field MRI apparatus) utilizing a hamburger type (open type) magnet having separated upper and lower magnets, which are used for increasing spaciousness. FIG. 1B shows an MRI apparatus 102 of the horizontal magnetic field type (horizontal magnetic field MRI apparatus) utilizing a tunnel-shaped magnet that generates a static magnetic field with a solenoid coil. Further, FIG. 1C shows an MRI apparatus 103 utilizing a tunnel-shaped magnet similar to that shown in FIG. 1B, but depth of the magnet is shortened and the magnet is leaned to increase spaciousness. The forms of these MRI apparatuses are mere examples of those of the vertical magnetic field type and the horizontal magnetic field type, and the MRI apparatus of the present invention is not limited to apparatuses having these forms.

The object of this embodiment is to obtain a magnetic susceptibility-weighted image ensuring high diagnostic ability regardless of the positional relationship of the $B_0$ direction of MRI apparatus and imaging slice. Therefore, in this embodiment, any of the aforementioned configurations of MRI apparatus may be used. Hereafter, this embodiment will be explained by exemplifying use of the vertical magnetic field MRI apparatus 101 shows in FIG. 1A. In the following explanation of this embodiment, there is used a coordinate system in which the $B_0$ direction of the MRI apparatus 101 is defined to be z direction, among two directions perpendicular to the z direction, the direction perpendicular to the body axis of the subject is defined to be x direction, and the direction parallel to the body axis of the subject to be y direction. Further, static magnetic field may also be henceforth referred to simply as magnetic field.

Figure 2:
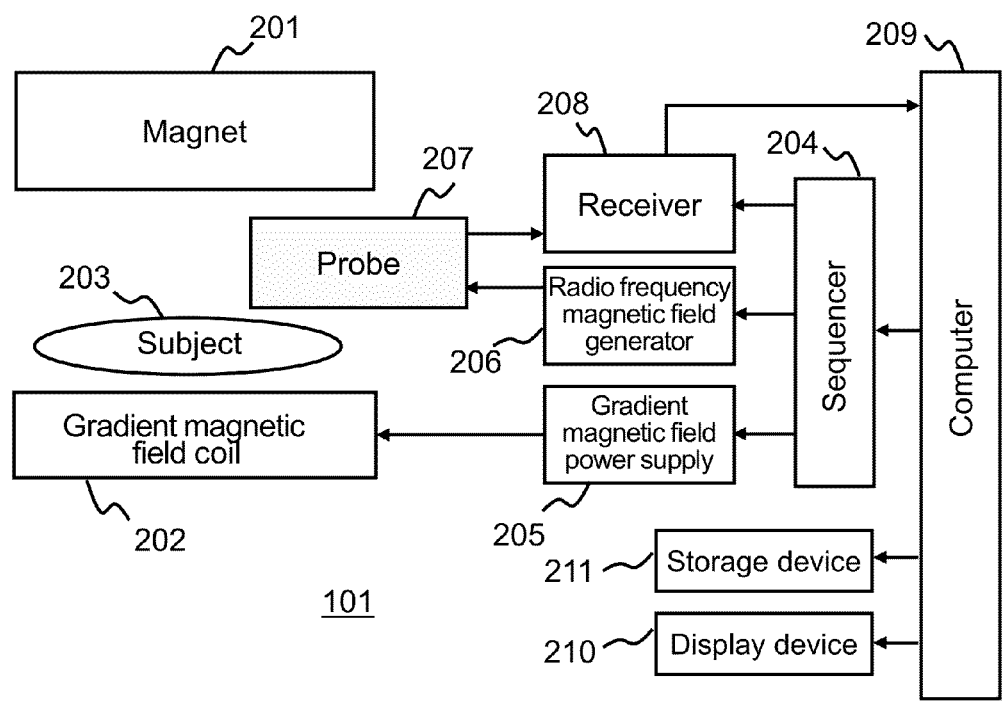
FIG. 2 is a block diagram showing schematic configuration of an MRI apparatus according to the first embodiment.

FIG. 2 is a block diagram showing the schematic configuration of the MRI apparatus 101 according to this embodiment. The MRI apparatus 101 is provided with a magnet 201 for generating a static magnetic field in a direction perpendicular to body axis of a subject, a gradient coil 202 for generating a gradient magnetic field, a sequencer 204, a gradient magnetic field power supply 205, a radio frequency magnetic field generator 206, a probe 207 for irradiating a radio frequency magnetic field and detecting a magnetic resonance signal (echo), a receiver 208, a computer 209, a display device 210, and a storage device 211. The subject 203 (for example, living body) is placed on a bed (table) or the like, and is placed in a static magnetic field space generated by the magnet 201.

The sequencer 204 sends commands to the gradient magnetic field power supply 205 and the radio frequency magnetic field generator 206 to make them generate a gradient magnetic field and a radio frequency magnetic field, respectively. The generated radio frequency magnetic field is irradiated on the subject 203 via the probe 207. Echoes generated from the subject 203 are received by the probe 207, and detected by the receiver 208. Nuclear magnetic resonance frequency as the basis of the detection (detection reference frequency $f_0$) is set by the sequencer 204. The detected signals are sent to the computer 209, and signal processing such as image reconstruction is performed by the computer. The results are displayed on the display device 210. The detected signals, measurement conditions, image information obtained after signal processing, and so forth may be stored in the storage device 211, as required.

The sequencer 204 controls the parts so that they operate at timings and intensities programmed beforehand. Among programs, a program describing timings and intensities of the radio frequency magnetic field, gradient magnetic field, and signal reception, in particular, is called a pulse sequence. Various pulse sequences suitable for various purposes are known. The MRI apparatus 101 according to this embodiment uses a pulse sequence of the GrE (gradient echo) type, which enables to obtain an image according to non-uniformity of spatial distribution of magnetic field intensity. The GrE type sequences include, for example, an RSSG (RF-spoiled-Steady-state Acquisition with Rewound Gradient-Echo) sequence.

The computer 209 according to this embodiment operates the parts of the MRI apparatus 101 according to the pulse sequence, measures echoes, and performs various processings described later for the measured echoes to obtain an image of a desired contrast.

Figure 3:
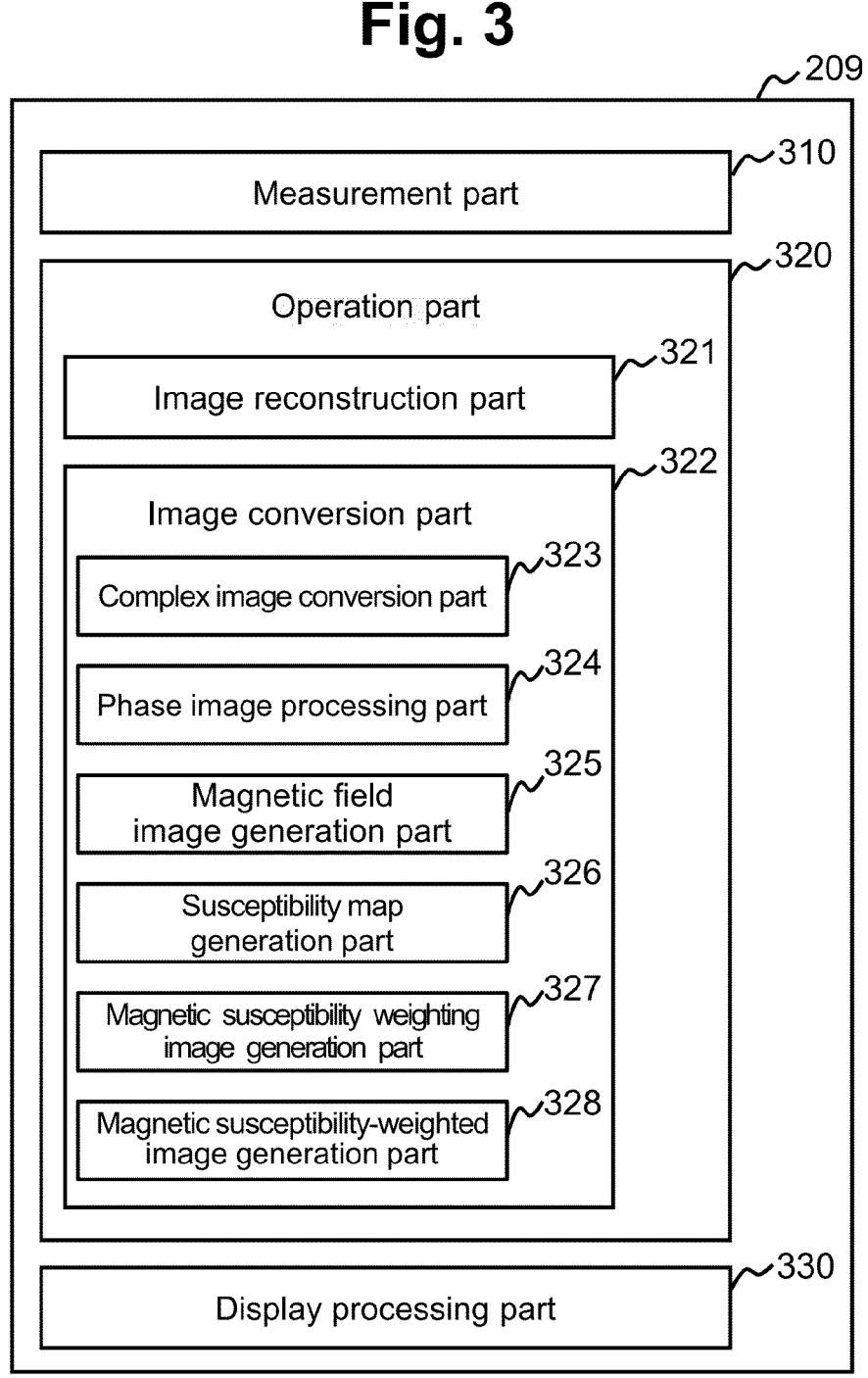
FIG. 3 is a functional block diagram of a computer according to the first embodiment.

In order to realize this image reconstruction, the computer 209 according to this embodiment is provided with, as shown in FIG. 3, a measurement part 310 for sending instructions for measuring echoes to the sequencer 204, and arranging the obtained echoes in the k-space, an operation part 320 for performing an operation for the echoes arranged in the k-space to generate an image, and a display processing part 330 for displaying the obtained image on the display device 210. Further, the operation part 320 is provided with an image reconstruction part 321 for reconstructing a complex image from the echoes arranged in the k-space, and an image conversion part 322 for performing a predetermined operation for the reconstructed complex image to create a magnetic susceptibility-weighted image.

These functions of the computer 209 are realized by CPU of the computer 209 by loading programs stored in the storage device 211 on a memory, and executing them.

Figure 4:
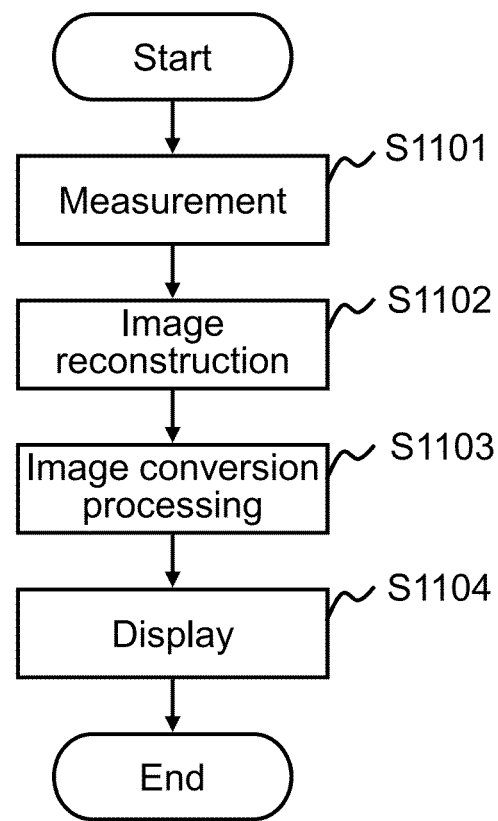
FIG. 4 is a flowchart of imaging processing according to the first embodiment.

First, the details of the imaging processing performed by the measurement part 310, the operation part 320 (the image reconstruction part 321 and the image conversion part 322), and the display processing part 330 of the computer 209 according to this embodiment will be explained with following the flow of the processing. FIG. 4 shows the process flow of the imaging processing according to this embodiment.

When various kinds of imaging conditions such as TE (echo time) are set, and a direction for starting imaging is received, the measurement part 310 performs the measurement (Step S1101). In this measurement, the measurement part 310 sends instructions to the sequencer 204 according to a pulse sequence defined beforehand to obtain echo signals and arranges them in a k-space. As described above, the sequencer 204 sends commands according to the instructions to the gradient magnetic field power supply 205 and the radio frequency magnetic field generator 206 to make them generate a gradient magnetic field and a radio frequency magnetic field, respectively. The echoes received by the probe 207 and detected by the receiver 208 are received as complex signals.

In the above process, a pulse sequence of the GrE type is used in this embodiment as described above. The methods for obtaining three-dimensional image information using a pulse sequence of the GrE type include a method of obtaining a plurality of two-dimensional images and a method of obtaining a three-dimensional image all at once, and either one of these methods may be used.

Figure 5:
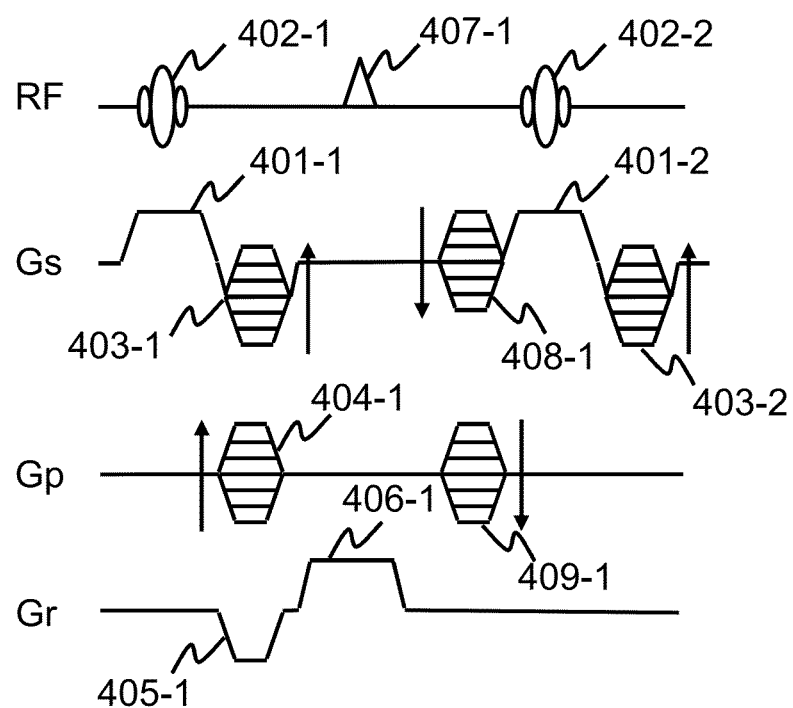
FIG. 5 is a pulse sequence diagram of an RSSG sequence.

The pulse sequence of the GrE type used in this embodiment will be explained below by referring to an RSSG sequence as an example. FIG. 5 is a pulse sequence diagram of the RSSG sequence. In this diagram, RF, Gs, Gp, and Gr represent radio frequency magnetic field, slice gradient magnetic field, phase encoding gradient magnetic field, and read-out gradient magnetic field, respectively. According to this embodiment, Gs is a gradient magnetic field of the y direction, Gp is a gradient magnetic field of the x direction, and Gr is a gradient magnetic field of the z direction.

With the RSSG sequence, a slice gradient magnetic field pulse 401 and a radio frequency magnetic field (RF) pulse 402 are simultaneously irradiated to excite magnetization in a predetermined slice of the subject 203. Then, a slice encoding gradient magnetic field pulse 403 and a phase encoding gradient magnetic field pulse 404 are applied for imparting positional information concerning the slice direction and the phase encoding direction to the phase of magnetization. After a read-out gradient magnetic field pulse 405 for dephasing for diffusing the phase of the nuclear magnetization in the pixels is applied, one magnetic resonance signal (echo) 407 is measured with applying a read-out gradient magnetic field pulse 406 for giving positional information concerning the read-out direction. Then, a slice encoding gradient magnetic field pulse 408 and a phase encoding gradient magnetic field pulse 409 for rephasing are finally applied. These are gradient magnetic field pulses for converging the phase of the nuclear magnetization dephased by the slice encoding gradient magnetic field pulse 403 and the phase encoding gradient magnetic field pulse 404.

The measurement part 310 repeatedly executes the above process at a cycle of the repetition time TR with changing the intensities of the slice encoding gradient magnetic field pulses 403 and 408 (slice encoding amount ks) and the phase encoding gradient magnetic field pulses 404 and 409 (phase encoding amount kp), and the phase of the RF pulse 402 to measure the echoes 407 required for obtaining one image. In the above process, the phase of the RF pulse 402 is increased by, for example, a unit of 117 degrees. In FIG. 5, the numerals mentioned after the hyphens indicate repetition times.

The measured echoes 407 are arranged in a three-dimensional k-space of which coordinate axis are kr, kp, and ks. In the k-space, one echo 407 constitutes one line parallel to the kr axis. If TE (time from the irradiation of the RF pulse 402 to the measurement of the echo 407) is set to be short, the absolute image obtained with this RSSG sequence becomes a T1 (longitudinal relaxation time)-weighted image, and if it is set to be long, the absolute image becomes a T2*-weighted image reflecting phase diffusion in the pixels.

After completion of the measurement, the image reconstruction part 321 performs an image reconstruction processing for reconstructing an image from the echoes arranged in the k-space (Step S1102). In this processing, the image reconstruction part 321 performs a processing such as three-dimensional inverse Fourier transform of the echoes (data) arranged in the k-space to reconstruct a complex image in which the pixel values are complex numbers.

The image conversion part 322 performs the various image conversion processings described later for the obtained complex image (Step S1103). According to this embodiment, the image conversion part 322 converts the complex image obtained with the image reconstruction part 321 into a magnetic susceptibility-weighted image. The details of the image conversion processing according to this embodiment will be described later.

Then, the display processing part 330 displays the obtained magnetic susceptibility-weighted image on the display device 210 as a gray-scale image (Step S1104). According to this embodiment, a plurality of images of continuous slices are subjected to the minIP processing, and then displayed. Information of a plurality of images may be unified by using another method, such as volume rendering, and displayed, or only one magnetic susceptibility-weighted image may be displayed.

The image conversion processing performed by the image conversion part 322 according to this embodiment will be explained below. As described above, the image conversion part 322 according to this embodiment performs the image conversion processing for obtaining a magnetic susceptibility-weighted image not depending on the $B_0$ direction. In advance of the explanation of the image conversion processing according to this embodiment, the image conversion processing according to the known SWI method and the $B_0$ direction dependency of a magnetic susceptibility-weighted image obtained thereby will be explained.

According to the SWI method, a processing for emphasizing the phase difference is performed for an absolute image by using a weighting image to create a magnetic susceptibility-weighted image. As the weighting image used for emphasizing the phase difference, a phase mask image created from a phase image is used. Therefore, the direction dependency of the phase image that the contrast changes depending on the $B_0$ direction is inherited as it is by the magnetic susceptibility-weighted image. In the following explanation, the $B_0$ direction dependency of the phase image will be explained first, and then the $B_0$ direction dependency of the magnetic susceptibility-weighted image obtained by the SWI method will be explained.

The relation between the phase and the magnetic field and the relation between the magnetic field and the magnetic susceptibility are represented by the equations (1) and (2), respectively. In the equations mentioned in this specification, r henceforth represents a vector having a size and a direction.

[Equation 1]

$$\phi(r) = -\frac{\delta(r)}{\gamma B_0 \tau_{TE}} \quad (1)$$

In the equation, $\phi(r)$ represents phase at a position r, $\delta(r)$ represents relative magnetic field intensity at the position r relative to a magnetic field intensity at an arbitrary position in the image as a reference, $\gamma$ represents magnetic rotation ratio, $B_0$ represents static magnetic field intensity, and $\tau_{TE}$ represents TE (echo time). $\gamma$ of proton as the object of imaging by MRI is $267.4 \times 10^6$ T$^{-1}$s$^{-1}$.

[Equation 2]

$$\delta(r) = \frac{1}{4\pi} \int \chi(r') \frac{3\cos^2\alpha - 1}{|r' - r|^3} d^3 r' \quad (2)$$

In the equation, $\chi(r)$ represents magnetic susceptibility at the position r in the image, and $\alpha$ is an angle between the $B_0$ direction of the vertical magnetic field type MRI apparatus (MRI apparatus 101) (z direction) and a vector (r'−r). Further, $\cos\alpha$ is represented by the following equation (3).

[Equation 3]

$$\cos\alpha = \frac{|r'_z - r_z|}{|r' - r|} \quad (3)$$

$r_z$ and $r'_z$ are z components of the vectors r and r', respectively.

The magnetic susceptibility distribution in a living body is always fixed regardless of the $B_0$ direction. However, the magnetic field distribution in a living body changes depending on the $B_0$ direction as represented by the equation (2). Therefore, as represented by the equation (1), pixel values of a phase image proportional to the magnetic field distribution also change depending on the $B_0$ direction. Therefore, in a phase image, contrast of a region and surrounding regions between which a magnetic susceptibility difference is generated changes depending on the $B_0$ direction. That is, in a phase image, contrast of a region and surrounding regions between which a magnetic susceptibility difference is generated changes depending on the $B_0$ direction.

As described above, according to the SWI method, a phase mask image in which signal intensities of negative phase regions are reduced is created by using a phase image, and an absolute image is multiplied with this phase mask image to obtain an image in which the negative phase regions are emphasized in black as a magnetic susceptibility-weighted image. Therefore, in a magnetic susceptibility-weighted image obtained by the SWI method, only regions having negative phase values are emphasized in black. Since the magnetic susceptibility-weighted image obtained by the SWI method is created by using a phase mask image created by using a phase image, contrast change thereof corresponds to the change of the contrast in the phase image.

Specific examples of dependency of the contrast of phase image on the $B_0$ direction are shown in FIGS. 6A to 7F. In these examples, the tissue to be emphasized (tissue of interest) is a vein. FIGS. 6A to 7F are drawings for explaining change of contrast in a phase image of a vein depending on the relation between the imaging slice direction and the $B_0$ direction. In these drawings, there are shown results of computer simulation where the imaging slice is an axial section, and the $B_0$ direction is the horizontal direction or the perpendicular direction.

Figures 6A, 6D:
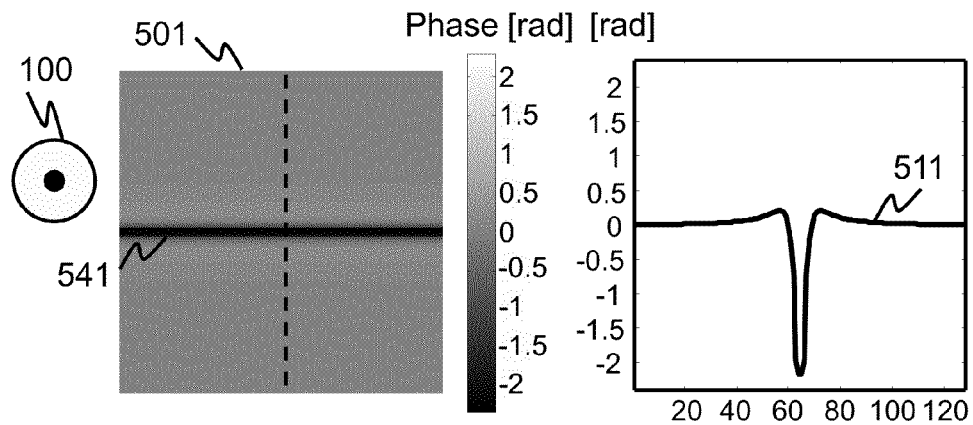
FIG. 6A is an explanatory drawing for explaining an example of phase image of an axial section obtained with a horizontal magnetic field MRI apparatus.
FIG. 6D is an explanatory drawing for explaining the luminance profile of the phase image shown in FIG. 6A.
Figures 6B, 6E:
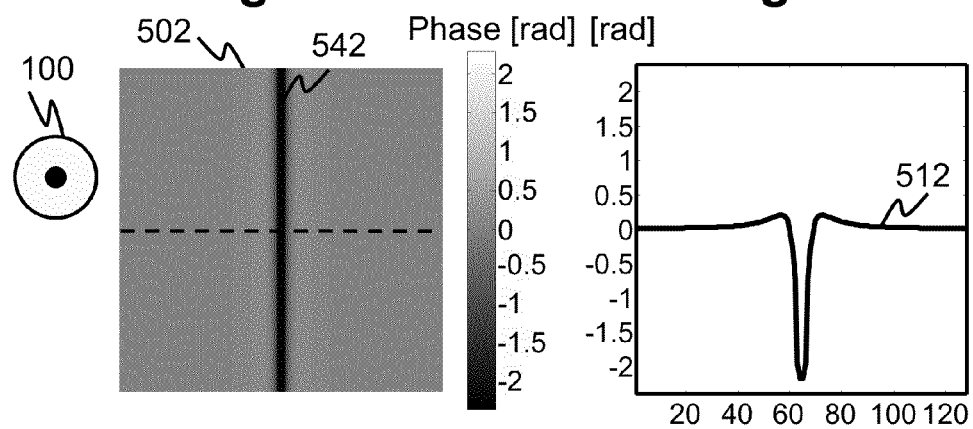
FIG. 6B is an explanatory drawing for explaining an example of phase image of an axial section obtained with a horizontal magnetic field MRI apparatus.
FIG. 6E is an explanatory drawing for explaining the luminance profile of the phase image shown in FIG. 6B.
Figures 6C, 6F:
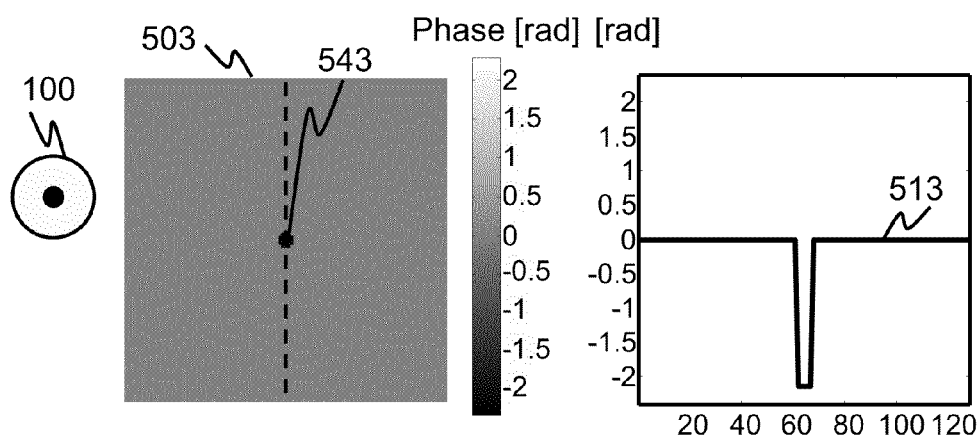
FIG. 6C is an explanatory drawing for explaining an example of phase image of an axial section obtained with a horizontal magnetic field MRI apparatus.
FIG. 6F is an explanatory drawing for explaining the luminance profile of the phase image shown in FIG. 6C.
Figures 7A, 7D:
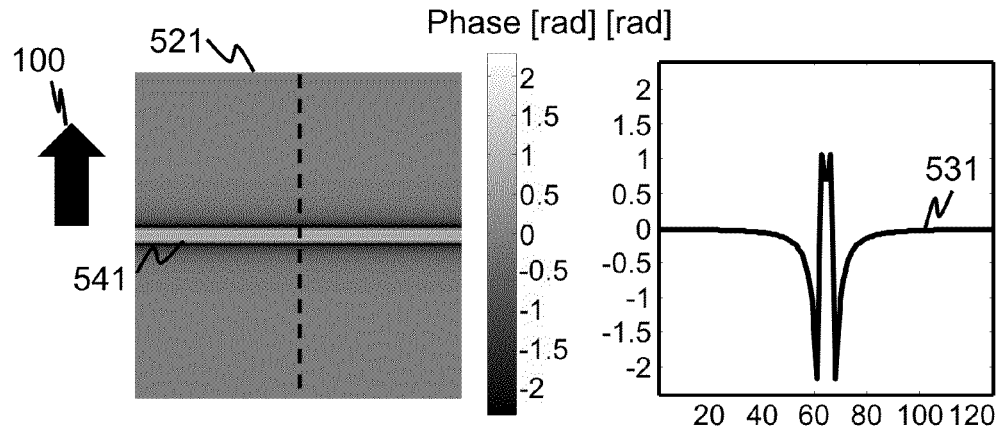
FIG. 7A is an explanatory drawing for explaining an example of phase image of an axial section obtained with a vertical magnetic field MRI apparatus.
FIG. 7D is an explanatory drawing for explaining the luminance profile of the phase image shown in FIG. 7A.
Figures 7B, 7E:
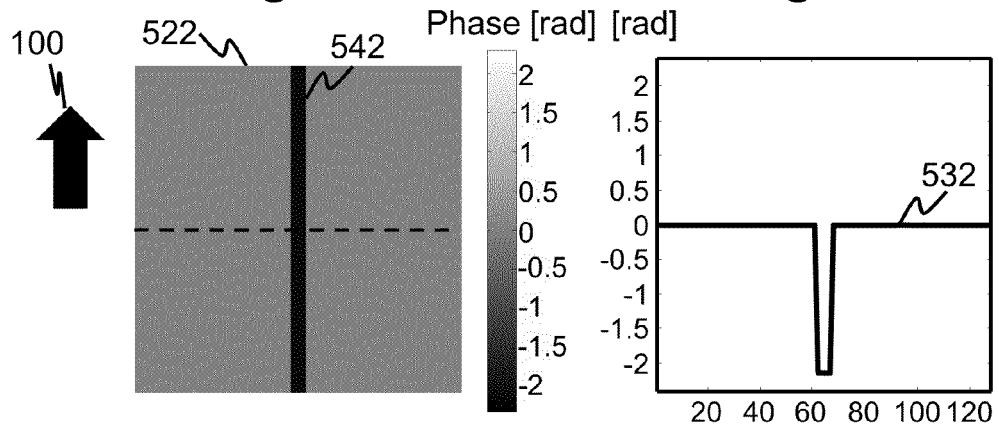
FIG. 7B is an explanatory drawing for explaining an example of phase image of an axial section obtained with a vertical magnetic field MRI apparatus.
FIG. 7E is an explanatory drawing for explaining the luminance profile of the phase image shown in FIG. 7B.
Figures 7C, 7F:
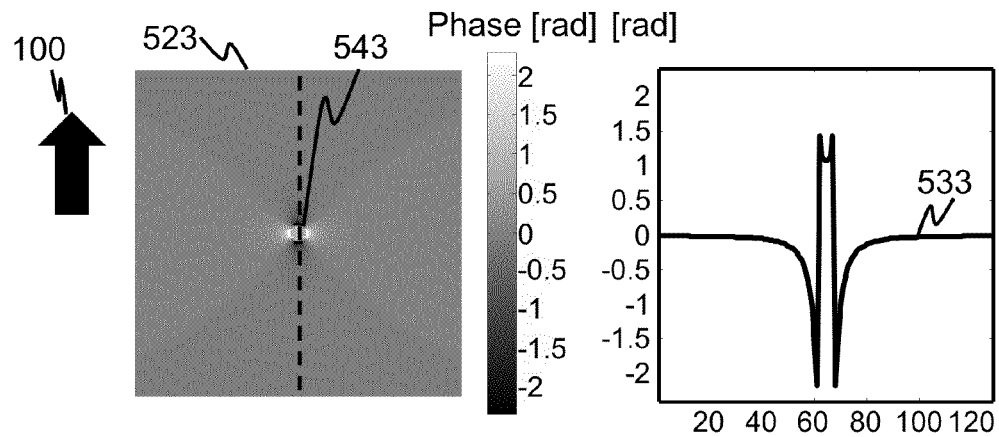
FIG. 7C is an explanatory drawing for explaining an example of phase image of an axial section obtained with a vertical magnetic field MRI apparatus.
FIG. 7F is an explanatory drawing for explaining the luminance profile of the phase image shown in FIG. 7C.

FIGS. 6A to 6C show phase images 501, 502, and 503 of axial sections obtained with the horizontal magnetic field MRI apparatus 102, and FIGS. 6D to 6F show luminance profiles 511, 512, and 513 of the line segments represented by the broken lines on the phase images 501, 502 and 503 shown in FIG. 6A to 6C, respectively. That is, FIGS. 6A to 6F show phase images and luminance profiles for the case where the imaging slice is perpendicular to the direction 100 of the static magnetic field. FIGS. 7A to 7C show phase images 521, 522, and 523 of axial sections obtained with the vertical magnetic field MRI apparatus 101, and FIGS. 7D to 7F show luminance profiles 531, 532, and 533 of the line segments represented by the broken lines on the phase images 521, 522 and 523 shown in FIG. 7A to 7C, respectively. That is, FIGS. 7A to 7F show phase images and luminance profiles for the case where the imaging slice is parallel to the $B_0$ direction. In FIGS. 6A to 6C, the direction perpendicular to the drawings is the direction 100 of the static magnetic field, and in FIGS. 7A to 7C, the up-and-down direction of the drawings is the direction 100 of the static magnetic field.

For both the cases of FIGS. 6A to 6C and FIGS. 7A to 7C, there were used three kinds of vein models, i.e., a vein model containing a vein 541 of which running direction is perpendicular to both the horizontal magnetic field and the vertical magnetic field (FIGS. 6A and 7A), a vein model containing a vein 542 of which running direction is parallel to the vertical magnetic field (FIGS. 6B and 7B), and a vein model containing a vein 543 of which running direction is parallel to the horizontal magnetic field (FIGS. 6C and 7C). All the images were obtained by the minIP processing of images for 10 slices. In these vein models, radius was supposed to be 3 pixels, extrevenous magnetic susceptibility to be 0 ppm, and intravenous magnetic susceptibility to be 0.4 ppm, and the simulation conditions consisted of a matrix size of 128×128×128, a static magnetic field intensity of 1.5 T, and TE of 40 ms. In the computer simulation, by using the aforementioned conditions, magnetic field images were calculated first from the susceptibility maps of the veins by using the equation (2), and then the phase images were calculated from the magnetic field images by using the equation (1).

As shown in the phase images 501, 502, and 503 of FIGS. 6A to 6C and the luminance profiles 511, 512, and 513 of FIGS. 6D to 6F, the insides of the veins 541, 542 and 543 of all the vein models are displayed with emphasis in black compared with the surrounding tissues in the phase images 501, 502, and 503 of the axial sections obtained with the horizontal magnetic field MRI apparatus 102. That is, the phases in the veins are negative for all the directions. On the other hand, as shown in the phase images 521, 522, and 523 of FIGS. 7A to 7C and the luminance profiles 531, 532, and 533 of FIGS. 7D to 7F, the inside of the vein 542 of the vein model parallel to the $B_0$ direction 100 is displayed with emphasis in black compared with the surrounding tissues, whereas the insides of the veins 541 and 543 of the vein models perpendicular to the $B_0$ direction 100 are not displayed with emphasis in black in the phase images 521, 522, and 523 of the axial sections obtained with the vertical magnetic field MRI apparatus 101. That is, the phases in the vein parallel to the $B_0$ direction 100 are negative, whereas the phases in the veins perpendicular to the $B_0$ direction 100 are positive.

As described above, the phase depends on the $B_0$ direction. The phase represents magnetic field distribution in the living body. On the other hand, magnetic susceptibility distribution in the living body does not depend on the $B_0$ direction, but is always fixed. This embodiment is based on this fact, and according to this embodiment, a processing for emphasizing magnetic susceptibility difference is performed on the basis of magnetic susceptibility distribution to create a magnetic susceptibility-weighted image.

In order to realize the above, the image conversion part 322 according to this embodiment is provided with a complex image conversion part 323, a phase image processing part 324, a magnetic field image generation part 325, a suscepti-bility map generation part 326, a magnetic susceptibility weighting image generation part 327, and a magnetic susceptibility-weighted image generation part 328, as shown in FIG. 3. Hereafter, the processings performed by these parts will be explained with following the flow of the image conversion processing performed by the image conversion part 322 according to this embodiment. FIG. 8 shows the process flow of the image conversion processing according to this embodiment.

When the image conversion processing is started, the complex image conversion part 323 first generates an absolute image and a phase image from the complex image generated by the image reconstruction part 321 (Step S1201). The absolute image and the phase image are created from the absolute value components and the phase components of the complex numbers of the pixels of the complex image, respectively.

Luminance value S(i) in the absolute image and luminance value $\phi(i)$ in the phase image of a pixel i are calculated in accordance with the equations (4) and (5), respectively, by using luminance value c(i) in the complex image. arg {z} represents declination of z.

[Equation 4]

$$S(i)=|c(i)| \quad (4)$$

[Equation 5]

$$\phi(i)=\arg\{c(i)\} \quad (5)$$

Then, the phase image processing part 324 performs a phase image processing defined beforehand for the phase image (Step S1202). According to this embodiment, three kinds of phase image processings are performed. The three kinds of phase image processings performed by the phase image processing part 324 according to this embodiment are explained with reference to the process flow shown in FIG. 9. However, the three kinds of processings mentioned below are mere examples, and the processing is not limited to these processings. Further, one or more of processings among these three kinds of processings may be omitted. Further, the order of the processings is not also limited.

First, the phase image processing part 324 performs a global phase change removal processing for removing global phase change from the phase image (Step S1301). The global phase change removal processing is a processing of calculating local phase changes resulting from magnetic susceptibility changes between tissues. This global phase change originates in non-uniformity of the static magnetic field generated depending on the shape of objective imaging part (for example, head etc.) and so forth, and corresponds to low frequency components in the spatial frequency region (k-space). According to this embodiment, a low pass filter processing is first performed for every two-dimensional image for the obtained three-dimensional image (original image) to calculate a low resolution image. Then, the global phase change contained in the low resolution image is removed from the original image by complex division of the original image with the low resolution image.

There are various known methods as the methods for removing global phase change. For example, other than the aforementioned method, there are a method of extracting global phase change by fitting of a three-dimensional image with a low order polynomial and subtracting it from an original image, and so forth. For the global phase change removal processing according to this embodiment, such another method may also be used.

Then, the phase image processing part 324 performs a phase unwrapping for correcting the wrapped phase (Step S1302). In a partial region of the phase image, phase values out of the range of −Π to Π are folded to be within the range of −Π to Π. According to this embodiment, phase values folded to be within the range of −Π to Π are corrected by using a known method such as the region growing method.

Then, the phase image processing part 324 performs a noise mask processing for regions containing only noise components (noise regions) in the phase image (Step S1303). The phase image processing part 324 first creates a mask image by using the absolute image. The mask image is created by defining pixel values of regions having values smaller than a predetermined threshold value to be 0, and pixel values of the other regions to be 1. Then, the phase image is multiplied by the created mask image.

There are various known methods of the noise mask processing. For example, a method of creating a mask image used for the noise mask processing by defining the pixel values of air regions to be 0 may be used. In this method, the phase image processing part 324 detects boundaries of the brain and air, and extracts air regions on the basis of the detection results. For the noise mask processing used in this embodiment, such another method as mentioned above may also be used.

In addition, the phase image processing may not necessarily be performed. In such a case, the image conversion part 322 may not have the phase image processing part 324.

Then, the magnetic field image generation part 325 generates a magnetic field image that represents spatial distribution of magnetic field intensity from the phase image (Step S1203). The magnetic field image is generated by using the relation of the phase and the magnetic field represented by the aforementioned equation (1). According to this embodiment, it is generated from the phase image obtained after the phase image processing performed by the phase image processing part 324. When the phase image processing is not performed, it is generated from the phase image created by the complex image conversion part 323.

Figure 10:
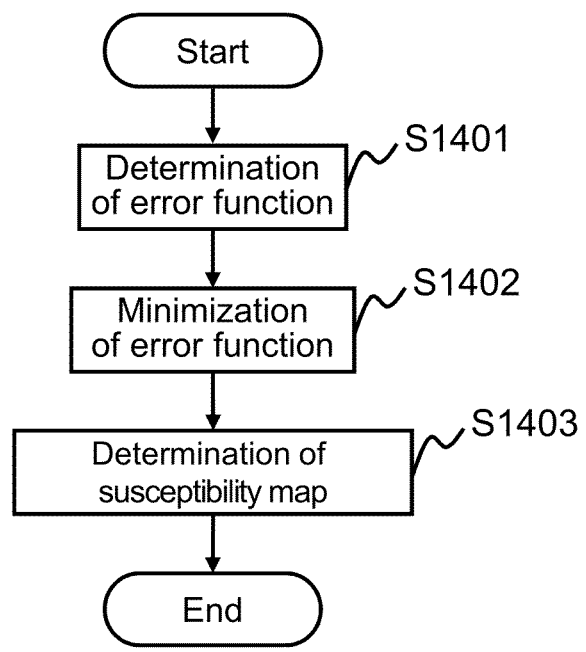
FIG. 10 is a flowchart of the susceptibility map generation processing according to the first embodiment.

The susceptibility map generation part 326 generates a susceptibility map from the magnetic field image (Step S1204). The method of the susceptibility map generation processing performed by the susceptibility map generation part 326 according to this embodiment will be explained with reference to the process flow shown in FIG. 10.

The susceptibility map generation part 326 first determines an error function representing difference between the calculated magnetic field image and a candidate of susceptibility map to be calculated (Step S1401). Then, it determines a susceptibility map candidate that minimizes the value of the error function (Step S1402), and defines the determined susceptibility map candidate to be the susceptibility map (Step S1403).

For the determination of the error function, the relation of the relative magnetic field intensity δ and the magnetic susceptibility χ represented by the equation (2) is used. If the equation (2) is expressed with a determinant for covering all the pixels in the magnetic field image as the object, it is expressed as the equation (6).

[Equation 6]

$$\delta = C\chi \quad (6)$$

In the equation, δ represents a column vector of a magnetic field image having a size of total pixel number N, and χ represents a column vector of a susceptibility map candidate. Further, C is a matrix having a size of N×N, and corresponding to convolution operation of χ.

The susceptibility map generation part 326 according to this embodiment calculates the susceptibility map by the least square method in accordance with the equation (6). For this purpose, the susceptibility map generation part 326 determines a susceptibility map candidate that minimizes the value of the error function e(χ) represented by the following equations (7) by using this function.

[Equation 7]

$$e(\chi) = |W \cdot (C\chi - \delta)|^2 \quad (7)$$

In the equation, W is a column vector having a size of N, and is a coefficient vector for weighting of the errors of the pixels. Further, · represents multiplication for every element of the vector, and |*| represents the norm of *.

According to this embodiment, the pixel values of the absolute image are used for the coefficient vector W in the equation (7). Specifically, a value W(i) of the coefficient vector for an arbitrary pixel i (i=1, 2, ..., N) is obtained in accordance with the following equation (8).

[Equation 8]

$$W(i) = \frac{S(i)}{S_{max}} \quad (8)$$

In the equation, S(i) is an absolute value (pixel value of the absolute image) of a pixel i, and $S_{max}$ is the maximum among all of the pixel values of the absolute image. As the signal-to-noise ratio (SN ratio) of the image becomes lower, variation of the phase caused by noises increases. By using the pixel values of the absolute image proportional to the SN ratio for the coefficient vector W, contribution of pixels showing large variations of phase to the error function can be reduced, and the accuracy of the susceptibility map χ to be calculated can be improved.

The error function to be calculated is not limited to those represented by the equations (7) and (8). For example, as the coefficient vector W, one in which the absolute image is raised to the n-th power (n is a positive real number), one in which only pixel values of the regions for which susceptibility maps are desired are defined to be 1, and the other pixel values to be 0, or the like may be used. Further, the function form of the error function e(χ) of the equation (7) may be changed. Various known function forms can be used, for example, a regularization term called L1 norm, or a more general regularization term called Lp norm (p>0) may be added to the equation (7).

The susceptibility map generation part 326 according to this embodiment minimizes the error to be calculated on the basis of the error function e(χ) by repetition of operation. According to this embodiment, the error function e(χ) is differentiated for χ, and χ making the value of the equation to be 0 is obtained. This equation can be developed into the equation (9).

[Equation 9]

$$C^* W^* \cdot W \cdot C\chi - C^* W^* \cdot W \cdot \delta = 0 \quad (9)$$

In this equation, C* and W* represent complex conjugate transposed matrixes of C and W, respectively. According to this embodiment, a solution of the equation (9) is calculated by the conjugate gradient method. The condition for ending repetition in the calculation by the conjugate gradient method according to this embodiment is based on the number of times of the repetition. As for the condition for ending repetition, the repetition may be ended when the relative residual difference $r_{rel}$ defined by the following equation (10) becomes a certain value or lower.

[Equation 10]

$$r_{rel} = \frac{|C^* W^* \cdot W \cdot C\chi - C^* W^* \cdot W \cdot \delta|}{|C^* W^* \cdot W \cdot \delta|} \quad (10)$$

In addition, there are various known methods for minimizing an error function such as the steepest descent method, and these other methods may also be used.

Further, for the calculation of the susceptibility map from the magnetic field image, a method other than the aforementioned method of minimizing the value of the error function may also be used. For example, the Fourier transform of the equation (6) may be carried out to obtain a susceptibility map in the Fourier space, and then it may be subjected to the inverse Fourier transform to obtain a susceptibility map in the real space.

Further, the measurement may be performed a plurality of times with various angles of the imaging region (for example, head) with respect to the fixed $B_0$ direction, and one susceptibility map may be calculated from the plurality of the obtained complex images. Variously changing the angle of the imaging region (for example, head) with respect to the fixed $B_0$ direction is equivalent to variously changing the $B_0$ direction applied to magnetic susceptibility distribution of an objective tissue of imaging (for example, brain tissue). Therefore, by these measurements, a plurality of magnetic field images for the case of applying the static magnetic field in different directions can be obtained. By calculating a susceptibility map from the plurality of these magnetic field images, the accuracy of the solution can be enhanced compared with the case of calculating the image from one magnetic field image. There are various known methods as the method for calculating a susceptibility map such as those mentioned above, and those methods can also be used.

The magnetic susceptibility weighting image generation part 327 generates a magnetic susceptibility weighting image as a weighting image from the susceptibility map (Step S1204). The magnetic susceptibility weighting image is a weighting image used for the weighting for emphasizing the contrast difference of the tissue of interest and surrounding tissues in the absolute image, in which signal intensities of regions of positive magnetic susceptibility are reduced to emphasize the magnetic susceptibility difference.

The object of the emphasis in the magnetic susceptibility-weighted image is, for example, a tissue containing a lot of paramagnetic substances such as veins. Such tissues show higher magnetic susceptibility compared with surrounding tissues. Therefore, for example, when the object of the imaging is brain, in the susceptibility map obtained with the susceptibility map generation part 326, the regions of veins shows a positive magnetic susceptibility value, whereas the magnetic susceptibility value is near 0 in the regions of the brain parenchyma as the surrounding tissues. Therefore, by performing weighting for the absolute image by using this magnetic susceptibility weighting image, an magnetic susceptibility-weighted image in which the contrast difference of the veins and the surrounding tissues is emphasized can be created.

Figure 11A:
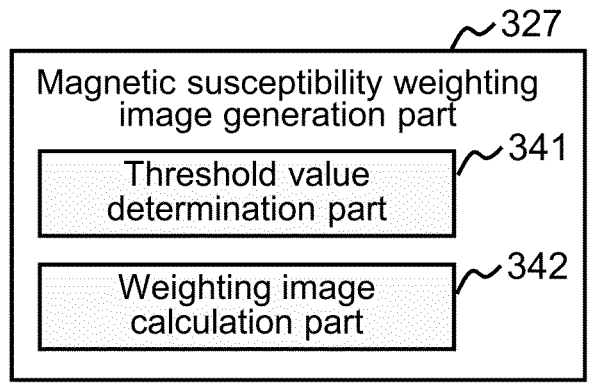
FIG. 11A is a functional block diagram of the magnetic susceptibility weighting image generation part according to the first embodiment.

In order to generate a magnetic susceptibility weighting image, the magnetic susceptibility weighting image generation part 327 is provided with a threshold value determination part 341 for determining one or more threshold values on the basis of luminance values of a susceptibility map, and a weighting image calculation part 342 for calculating a magnetic susceptibility weighting image by using the susceptibility map and the threshold value or values determined by the threshold value determination part 341, as shown in FIG. 11A. The magnetic susceptibility weighting image generation part 327 according to this embodiment calculates weights of pixels of the magnetic susceptibility weighting image by using these functions.

The threshold value determination part 341 determines two of threshold values, a first threshold value and a second threshold value, on the basis of luminance values of the susceptibility map. The second threshold value is a value larger than the first threshold value. According to this embodiment, the first threshold value is defined to be, for example, 0, and the second threshold value $\chi_M$ is defined as a value corresponding to the threshold value Π of the phase image mask used in the SWI method. The first threshold value and the second threshold value are set to be such values that the contrast difference of a tissue of interest and surrounding tissues becomes large, and noises of the whole image does not become large in the final magnetic susceptibility-weighted image.

For example, a histogram of the pixel values of the phase image (phase histogram) and a histogram of the pixel values of the susceptibility map (magnetic susceptibility histogram) are calculated. Then, from these phase histogram and magnetic susceptibility histogram, a standard deviation $\sigma_p$ of the phase histogram, and a standard deviation $\sigma_x$ of the magnetic susceptibility histogram are obtained, respectively, by curve fitting or the like. Finally, from the threshold value Π of the phase image mask, and the obtained $\sigma_p$, and $\sigma_x$, the second threshold value $\chi_M$ is calculated in accordance with the equation (11).

[Equation 11]

$$\chi_M = \pi \cdot \frac{\sigma_x}{\sigma_p} \quad (11)$$

Figure 11B:
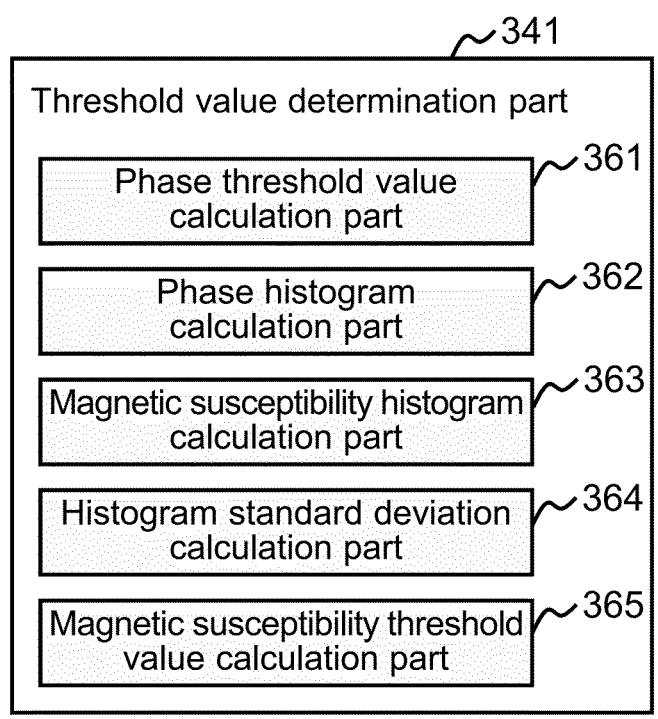
FIG. 11B is a functional block diagram of the threshold value determination part according to the first embodiment.

That is, in such a case as mentioned above, as shown in FIG. 11B, the threshold value determination part 341 is provided with a phase threshold value calculation part 361 for determining one or more phase threshold values from the pixel values of the phase image, a phase histogram calculation part 362 for calculating a phase histogram as a histogram of the pixel values of the phase image, a magnetic susceptibility histogram calculation part 363 for calculating a magnetic susceptibility histogram as a histogram of the pixel values of the susceptibility map, a histogram standard deviation calculation part 364 for calculating standard deviations of the phase histogram and the magnetic susceptibility histogram, and a magnetic susceptibility threshold value calculation part 365 for calculating one or more magnetic susceptibility threshold values using the phase threshold value or values, the standard deviation of the phase histogram, and the standard deviation of the magnetic susceptibility histogram.

The weighting image calculation part 342 converts the pixel values of the susceptibility map into weight values by using the first threshold value and the second threshold value.

In this procedure, as for the pixels of the susceptibility map, weights of the pixels having a luminance value smaller than the first threshold value are set to be a predetermined constant (first weight value), weights of the pixels having a luminance value larger than the second threshold value are set to be a predetermined constant different from the first weight value (second weight value), and weights of the pixels having a luminance value between the first threshold value and the second threshold value are set to be a value calculated according to a predetermined function connecting the first weight value and the second weight value (third weight value).

For example, if the first threshold value is defined to be 0, the first weight value to be 1, and the second weight value to be 0, a pixel value M(i) of each pixel i of the weighting image is calculated in accordance with the following equation (12).

[Equation 12]

$$M(i) = \begin{cases} 1 & (\chi(i) < 0) \\ 0 & (\chi(i) > \chi_M) \\ -\chi(i)/\chi_M + 1 & (0 \le \chi(i) \le \chi_M) \end{cases} \quad (12)$$

The magnetic susceptibility weighting image obtained in accordance with the equation (12) may be raised to the Nm-th power (Nm is a positive integer).

Further, only one threshold value may be used for the calculation of the weighting image. When one threshold value is used, the weighting image calculation part 342 calculates the pixel value M(i) of each pixel i of the weighting image for emphasizing the contrast difference between two kinds of tissues in accordance with the following equations (13).

[Equation 13]

$$M(i) = \frac{1 \pm \tanh\{\chi(i) - \chi'_M\}}{2} \quad (13)$$

In the equation, $\chi'_M$ is a predetermined threshold value. This threshold value is defined according to the magnetic susceptibilities of two kinds of tissues for which emphasis of the contrast difference is desired.

The method for calculating a magnetic susceptibility weighting image from the susceptibility map can be freely chosen according to the characteristics of a region or tissue to be emphasized in the magnetic susceptibility-weighted image to be finally obtained. For example, it is known that a region of a living body in which calcium salts deposit to cause calcification has a negative magnetic susceptibility value. When it is desired to emphasize such a region in black in the magnetic susceptibility-weighted image, the aforementioned threshold values and weight values are determined so that the signal intensities of regions showing a negative magnetic susceptibility value are reduced.

Then, the magnetic susceptibility-weighted image generation part 328 generates a magnetic susceptibility-weighted image from the absolute image by using the magnetic susceptibility weighting image (Step S1206). According to this embodiment, the absolute image is multiplied by the weighting image to obtain a magnetic susceptibility-weighted image. That is, the pixel value E(i) of the pixel i in the magnetic susceptibility-weighted image is calculated in accordance with the equation (14).

[Equation 14]

$$E(i) = M(i) \times S(i) \quad (14)$$

In the equation, M(i) is a pixel value of the pixel i in the magnetic susceptibility weighting image, and S(i) is a pixel value in the absolute image.

As explained above, the magnetic susceptibility-weighted image is generated by the image conversion part 322 according to this embodiment using magnetic susceptibility distribution not depending on the $B_0$ direction. Therefore, veins can be emphasized regardless of the $B_0$ direction. Examples of magnetic susceptibility-weighted image obtained by the conventional SWI method and magnetic susceptibility-weighted image obtained with the image conversion part 322 according to this embodiment are shown below.

Figure 12A:
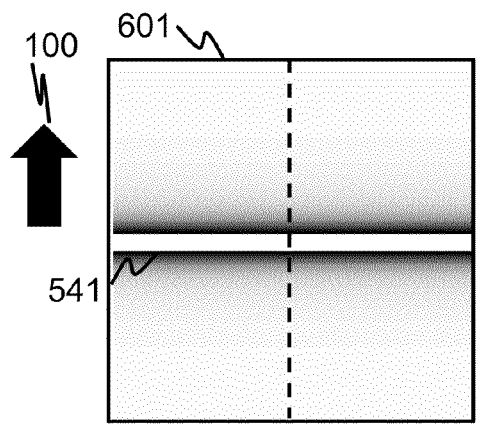
FIG. 12A is an explanatory drawing for explaining an example of magnetic susceptibility-weighted image formed by the SWI method.
Figure 12B:
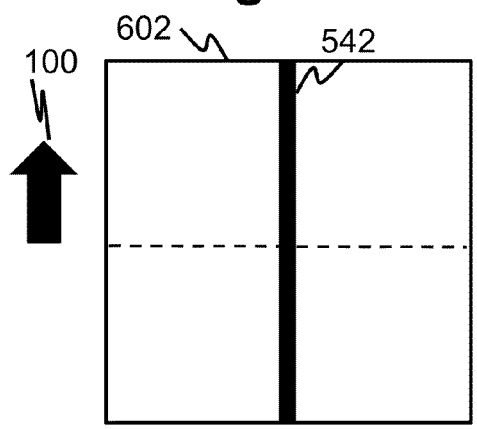
FIG. 12B is an explanatory drawing for explaining an example of magnetic susceptibility-weighted image formed by the SWI method.
Figure 12C:
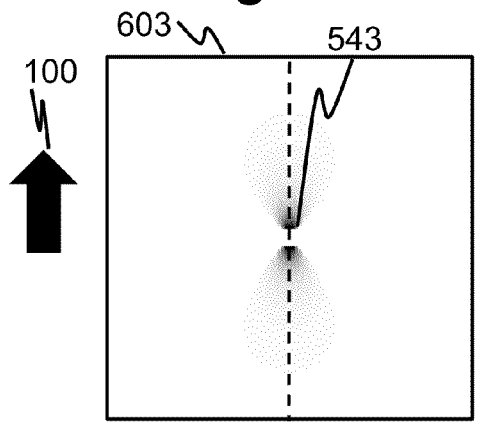
FIG. 12C is an explanatory drawing for explaining an example of magnetic susceptibility-weighted image formed by the SWI method.
Figure 12D:
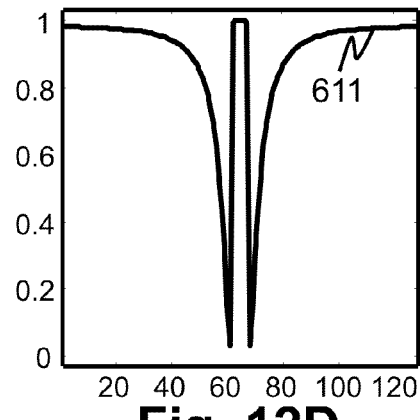
FIG. 12D is an explanatory drawing for explaining the luminance profile of the magnetic susceptibility-weighted image shown in FIG. 12A.
Figure 12E:
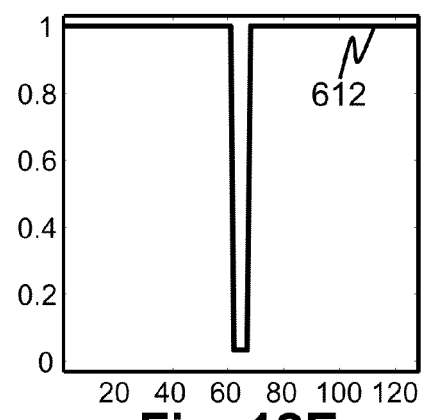
FIG. 12E is an explanatory drawing for explaining the luminance profile of the magnetic susceptibility-weighted image shown in FIG. 12B.
Figure 12F:
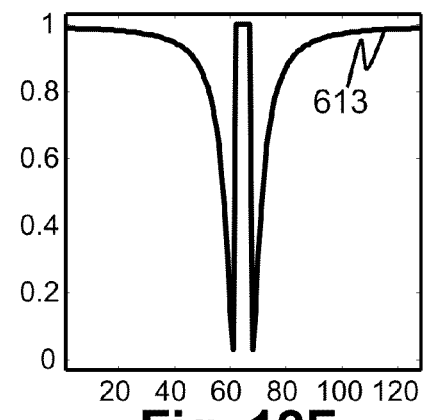
FIG. 12F is an explanatory drawing for explaining the luminance profile of the magnetic susceptibility-weighted image shown in FIG. 12C.
Figure 13A:
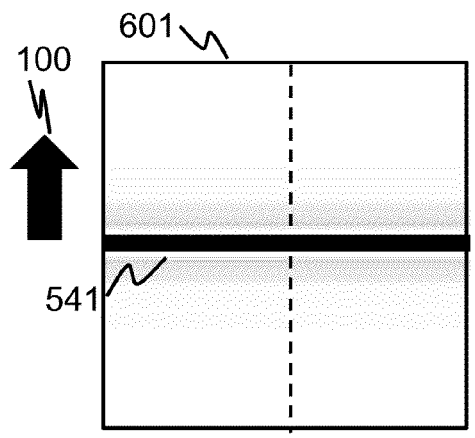
FIG. 13A is an explanatory drawing for explaining an example of magnetic susceptibility-weighted image obtained by the image conversion processing according to the first embodiment.
Figure 13D:
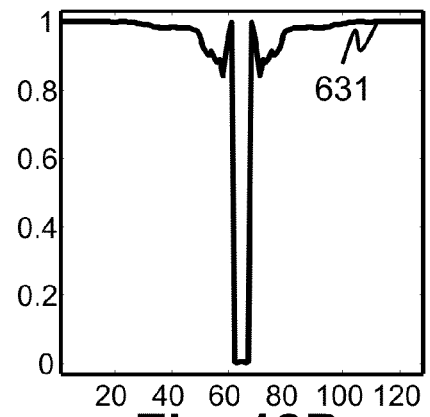
FIG. 13D is an explanatory drawing for explaining the luminance profile of the magnetic susceptibility-weighted image shown in FIG. 13A.
Figure 13B:
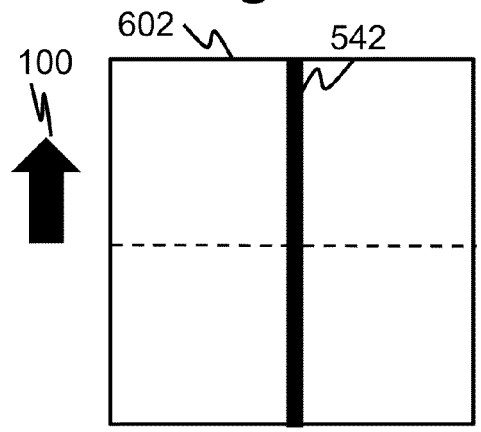
FIG. 13B is an explanatory drawing for explaining an example of magnetic susceptibility-weighted image obtained by the image conversion processing according to the first embodiment.
Figure 13E:
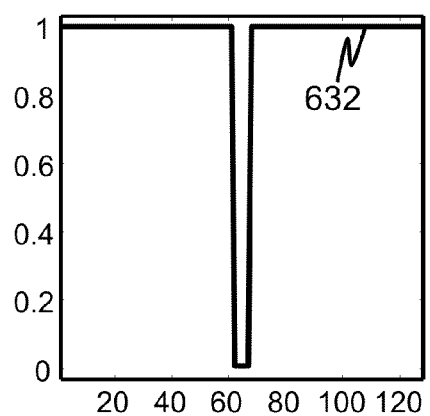
FIG. 13E is an explanatory drawing for explaining the luminance profile of the magnetic susceptibility-weighted image shown in FIG. 13B.
Figure 13C:
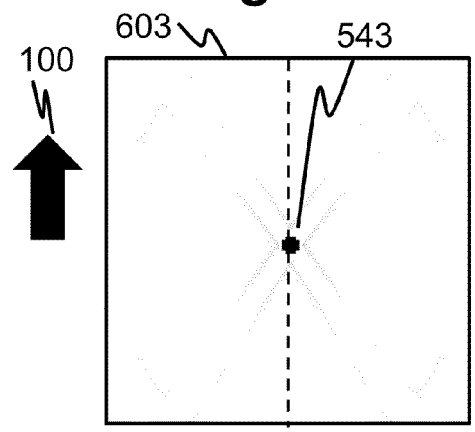
FIG. 13C is an explanatory drawing for explaining an example of magnetic susceptibility-weighted image obtained by the image conversion processing according to the first embodiment.
Figure 13F:
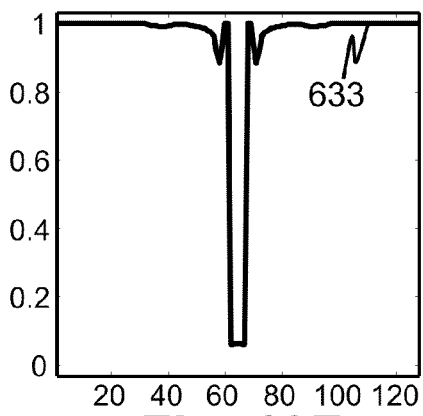
FIG. 13F is an explanatory drawing for explaining the luminance profile of the magnetic susceptibility-weighted image shown in FIG. 13C.

FIGS. 12A to 13F show magnetic susceptibility-weighted images of a vein calculated by computer simulation. FIGS. 12A to 12C show magnetic susceptibility-weighted images 601, 602, and 603 obtained by performing the image conversion processing according to the SWI method for the phase images of three veins 541, 542, and 543 shown in FIGS. 7A to 7C, respectively. FIGS. 13A to 13C show magnetic susceptibility-weighted images 621, 622, and 623 obtained by performing the image conversion processing according to this embodiment for the phase images of three veins 541, 542, and 543 shown in FIGS. 7A to 7C, respectively. All the images are obtained by the minIP processing of images of 10 slices. Further, FIGS. 12D to 12F show luminance profiles 611, 612, and 613 of the line segments indicated with the broken lines on the magnetic susceptibility-weighted images 601, 602, and 603 shown in FIGS. 12A to 12C, and FIGS. 13D to 13F show luminance profiles 631, 632, and 633 of the line segments indicated with the broken lines shown in FIGS. 13A to 13C.

In the image conversion processing used for all the images of FIGS. 12A to 12C and FIGS. 13A to 13C, the pixel values of the absolute images of the insides and outsides of the veins were assumed to be 1. Further, in the image conversion processing according to this embodiment for obtaining the magnetic susceptibility-weighted images 621, 622, and 623 shown in FIGS. 13A to 13C, the number of times of repetition for obtaining a susceptibility map was set to be 200 times, and the number of times Nm of the multiplication by the magnetic susceptibility weighting image was set to be 3 times.

The magnetic susceptibility-weighted images 601, 602, and 603 created by the SWI method (or the luminance profiles 611, 612, and 613) are compared with the magnetic susceptibility-weighted images 621, 622, and 623 created according to this embodiment (or the luminance profiles 631, 632, and 633). As seen from comparison of the image 602 and the image 622 (or comparison of the luminance profiles 612 and 632), the inside of the vein 542 substantially parallel to the $B_0$ direction is emphasized in black both in the magnetic susceptibility-weighted image obtained by the SWI method and the magnetic susceptibility-weighted image obtained according to this embodiment. On the other hand, as seen from comparison of the image 601 and the image 621 (or comparison of the luminance profiles 611 and 621), and comparison of the image 603 and the image 623 (or comparison of the luminance profiles 613 and 623), the insides of the veins 541 and 543 perpendicular to the $B_0$ direction are not emphasized in black in the magnetic susceptibility-weighted images obtained by the SWI method. However, the insides of the veins 541 and 543 perpendicular to the $B_0$ direction are also emphasized in black in the magnetic susceptibility-weighted images obtained according to this embodiment.

This result indicates that the magnetic susceptibility-weighted images obtained by the SWI method suffer from a $B_0$ direction dependency, in which a vein perpendicular to the $B_0$ direction is not emphasized, but the magnetic susceptibility-weighted images obtained according to this embodiment do not show such $B_0$ direction dependency, in which a vein of any direction is emphasized.

As explained above, the magnetic resonance imaging apparatus 101 according to this embodiment comprises the measurement part 310 for applying a radio frequency magnetic field and a gradient magnetic field to the subject 203 placed in a static magnetic field and detecting magnetic resonance signals generated from the subject 203 as complex signals, the operation part 320 for performing an operation for the complex signals to generate an image, and the display processing part 330 for displaying the generated image on the display device 210, wherein the operation part 320 comprises the image reconstruction part 321 for reconstructing a complex image in which pixel values are complex numbers from the complex signals, and the image conversion part 322 for converting the complex image into a magnetic susceptibility-weighted image, and the image conversion part 322 comprises the complex image conversion part 323 for generating an absolute image and a phase image from absolute value components and phase components of the complex numbers of pixels of the complex image, respectively, the magnetic field image generation part 325 for generating a magnetic field image representing spatial distribution of magnetic field intensity from the phase image, the susceptibility map generation part 326 for generating a susceptibility map from the magnetic field image, the magnetic susceptibility weighting image generation part 327 for generating a weighting image for performing weighting for emphasizing contrast difference of a tissue of interest and surrounding tissues from the susceptibility map, and the magnetic susceptibility-weighted image generation part 328 for generating a magnetic susceptibility-weighted image by multiplication of the absolute image and the weighting image.

The weighting image may be a magnetic susceptibility weighting image for emphasizing magnetic susceptibility difference, and the magnetic susceptibility weighting image generation part 327 may comprises the threshold value determination part 341 for determining one or more threshold values based on luminance values of the susceptibility map, and the weighting image calculation part 342 for calculating the weighting image from the susceptibility map and the magnetic susceptibility threshold value or values determined by the threshold value determination part 341.

Further, the threshold value determination part 341 may determine a first magnetic susceptibility threshold value and a second magnetic susceptibility threshold value having a value larger than the first magnetic susceptibility threshold value on the basis of luminance values of the susceptibility map, and for pixels of the susceptibility map, the weighting image calculation part 342 may define weights of pixels having a luminance value smaller than the first magnetic susceptibility threshold value to be a predetermined first weight value, define weights of pixels having a luminance value larger than the second magnetic susceptibility threshold value to be a predetermined second weight value different from the first weight value, and define weights of pixels having a luminance value between the first magnetic susceptibility threshold value and the second magnetic susceptibility threshold value to be a value calculated according to a predetermined function connecting the first weight value and the second weight value.

Further, the threshold value determination part 341 may comprise the phase threshold value calculation part 361 for determining one or more phase threshold values on the basis of the pixel values of the phase image, the phase histogram calculation part 362 for calculating a phase histogram as a histogram of the pixel values of the phase image, the magnetic susceptibility histogram calculation part 363 for calculating a magnetic susceptibility histogram as a histogram of the pixel values of the susceptibility map, the histogram standard deviation calculation part 364 for calculating standard deviations of the phase histogram and the magnetic susceptibility histogram, and the magnetic susceptibility threshold value calculation part 365 for calculating one or more of the magnetic susceptibility threshold values on the basis of the phase threshold value or values, the standard deviation of the phase histogram, and the standard deviation of the magnetic susceptibility histogram.

According to this embodiment, a phase image is converted into a susceptibility map not depending on the $B_0$ direction, and then a weighting image used for weighting is generated by using the susceptibility map as described above. The generated weighting image is an image for emphasizing contrast difference of a tissue of interest and surrounding tissues. Further, by multiplication of the weighting image and the absolute image, a magnetic susceptibility-weighted image is obtained.

Therefore, according to this embodiment, weighting is performed on the basis of the susceptibility map not depending on the $B_0$ direction, and therefore a magnetic susceptibility-weighted image not suffering from $B_0$ direction dependency can be obtained.

Since contrast in the magnetic susceptibility-weighted image obtained according to this embodiment is not depending on the $B_0$ direction, an object desired to be emphasized in a magnetic susceptibility-weighted image, such as vein, can be emphasized for an arbitrary imaging slice regardless of the direction of the magnetic field of the MRI apparatus. Although the above embodiment was basically explained by exemplifying an example where the imaging slice is an axial section, the same effect can be obtained even when the imaging slice is, for example, a coronal section, a sagittal section, an oblique section, or the like.

It will be explained below that even if the imaging slice is a coronal section, a magnetic susceptibility-weighted image in which an object desired to be emphasized is emphasized can be obtained regardless of the direction of the magnetic field of the MRI apparatus by applying the image conversion processing according to this embodiment. For this purpose, computer simulation results are shown below for the case of obtaining a magnetic susceptibility-weighted image of a coronal section by using the horizontal magnetic field MRI apparatus 102.

Figure 14A:
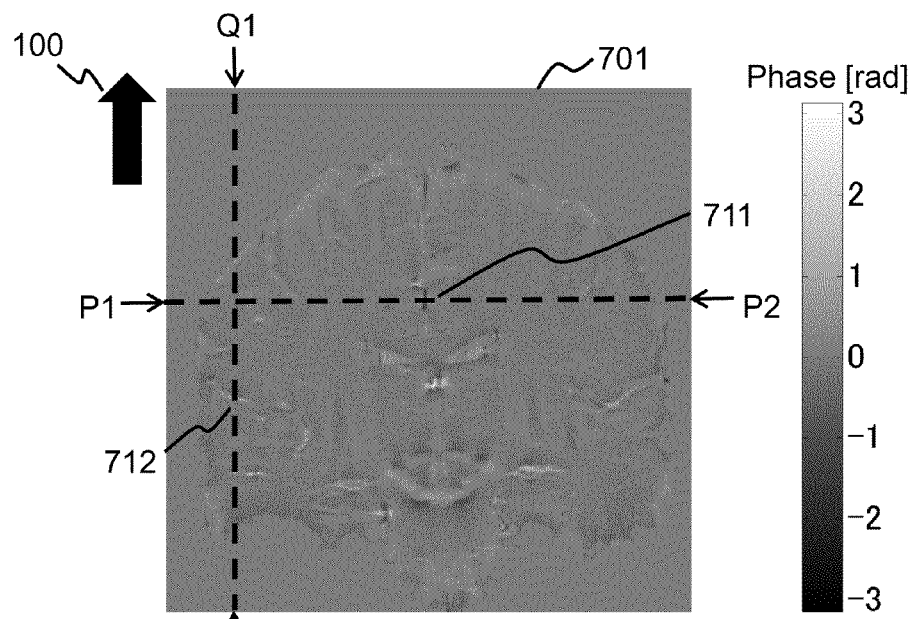
FIG. 14A is an explanatory drawing for explaining a phase image of a coronal section obtained with a horizontal magnetic field MRI apparatus.
Figure 14B:
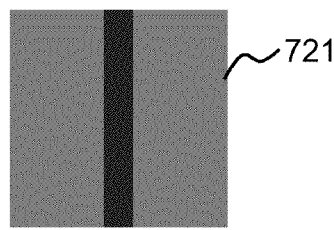
FIG. 14B is an explanatory drawing for explaining outline of a phase image of a vein on a coronal section obtained with a horizontal magnetic field MRI apparatus.
Figure 14C:
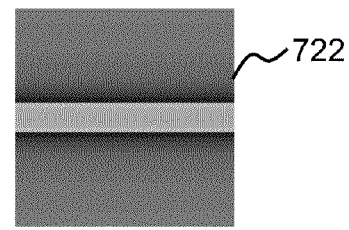
FIG. 14C is an explanatory drawing for explaining outline of a phase image of a vein on a coronal section obtained with a horizontal magnetic field MRI apparatus.
Figure 14D:
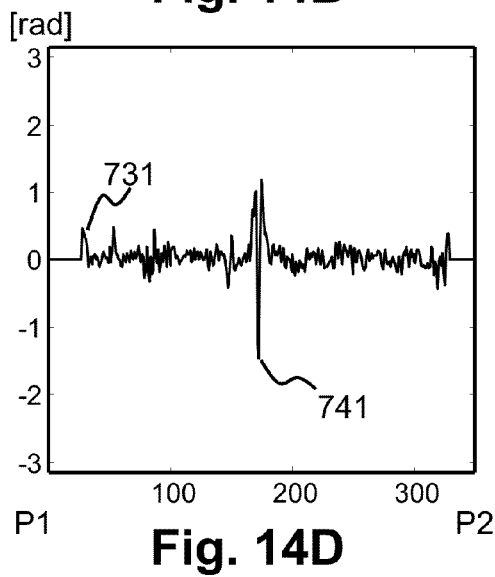
FIG. 14D is an explanatory drawing for explaining the luminance profile of the image shown in FIG. 14A.
Figure 14E:
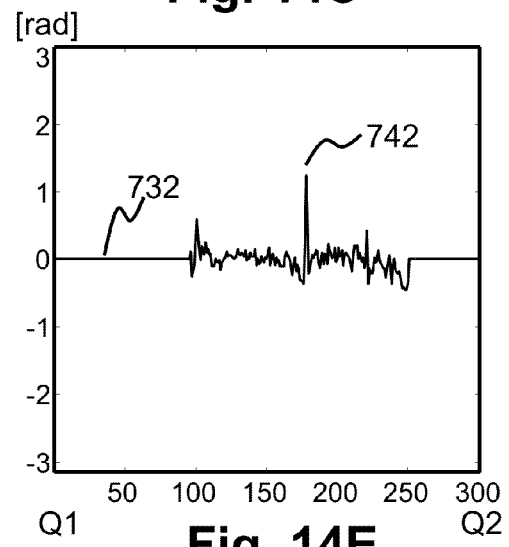
FIG. 14E is an explanatory drawing for explaining the luminance profile of the image shown in FIG. 14A.

Before explaining the effect of this embodiment for the case of using the horizontal magnetic field MRI apparatus 102, a phase image of a coronal section obtained with the horizontal magnetic field MRI apparatus 102 will be explained. FIG. 14A shows a phase image 701 of a coronal section obtained with the horizontal magnetic field MRI apparatus 102, FIG. 14B shows a schematic diagram 721 of a phase image of a vein 711 of which running direction is approximately parallel to the direction 100 of the static magnetic field, FIG. 14C shows a schematic diagram 722 of a phase image of a vein 712 of which running direction is approximately perpendicular to the $B_0$ direction, FIG. 14D shows a luminance profile 731 of the line segment between P1 and P2 on the phase image 701 shown in FIG. 14A, and FIG. 14E show a luminance profile 732 of the line segment between Q1 and Q2 on the phase image 701 shown in FIG. 14A.

The phase of the vein 711 approximately parallel to the direction 100 of the static magnetic field is negative (black) as shown in the schematic diagram 721, whereas the phase of the vein 712 approximately perpendicular to the direction 100 of the static magnetic field is positive (white) as shown in the schematic diagram 722. Also in the luminance profiles 731 and 732, the luminance 741 of the vein 711 is negative, and the luminance 742 of the vein 712 is positive. In the magnetic susceptibility-weighted image obtained by the SWI method, only a region of a negative phase is emphasized in black. Therefore, in the magnetic susceptibility-weighted image obtained by the SWI method, only a vein approximately parallel to the direction 100 of the static magnetic field is emphasized.

In contrast, the magnetic susceptibility-weighted image obtained according to this embodiment is obtained by using magnetic susceptibility distribution not depending on the $B_0$ direction, and therefore contrast difference of a vein and surrounding tissues can be emphasized regardless of the $B_0$ direction. Examples of these cases are shown in FIGS. 15A to 16C.

Figure 16A:
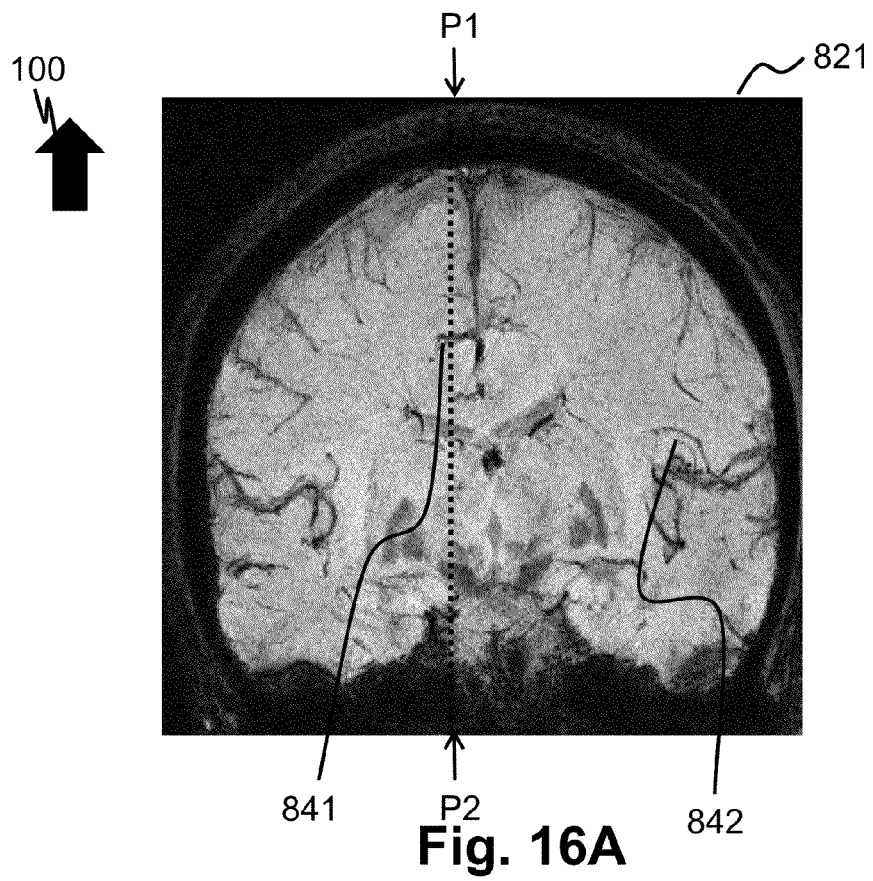
FIG. 16A is an explanatory drawing for explaining an example of magnetic susceptibility-weighted image obtained by the image conversion processing according to the first embodiment.
Figure 16B:
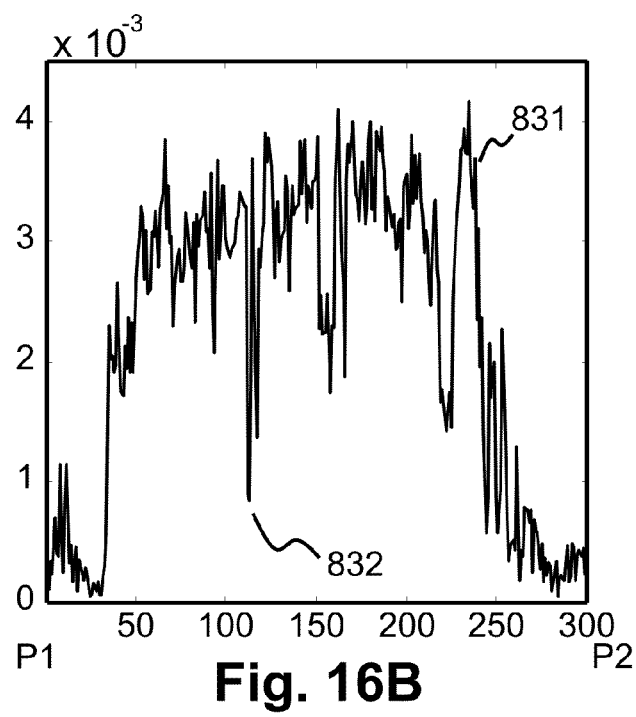
FIG. 16B is an explanatory drawing for explaining the luminance profile of the magnetic susceptibility-weighted image shown in FIG. 16A.
Figure 16C:
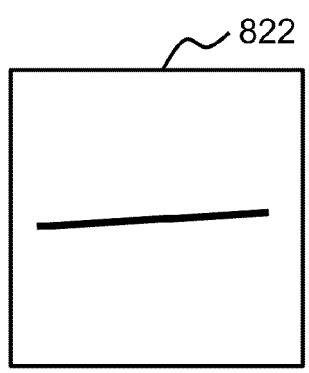
FIG. 16C is an explanatory drawing for explaining the vein imaging ability in the magnetic susceptibility-weighted image obtained by the image conversion processing according to the first embodiment.

FIGS. 15A and 16A show a magnetic susceptibility-weighted image 801 created by the image conversion process according to the SWI method and a magnetic susceptibility-weighted image 821 created by the image conversion processing according to this embodiment from an image of a coronal section obtained with the horizontal magnetic field MRI apparatus 102, respectively. FIGS. 15B and 16B show luminance profiles 811 and 831 of the line segments between P1 and P2 on the magnetic susceptibility-weighted image 801 and the magnetic susceptibility-weighted image 821, respectively, and FIGS. 15C and 16C show schematic diagrams 802 and 822 for explaining the vein depiction abilities of the magnetic susceptibility-weighted image 801 and the magnetic susceptibility-weighted image 821, respectively.

The magnetic susceptibility-weighted image 801 and the magnetic susceptibility-weighted image 821 were each obtained by the minIP processing of the images of 10 slices among 20 complex images subjected to the image conversion processing according to the SWI method or the image conversion processing according to this embodiment, out of 80 images obtain with a pulse sequence of the GrE type. As for the image conversion processing of the magnetic susceptibility-weighted image 821, the number of times of repetition for obtaining the susceptibility map was 150 times, and the number of times Nm of the multiplication by the magnetic susceptibility weighting image was 3 times.

The magnetic susceptibility-weighted image 801 created by the image conversion processing according to the SWI method is compared with the magnetic susceptibility-weighted image 821 created by the image conversion processing according to this embodiment. In this comparison, displays of the vein 841 perpendicular to the direction 100 of the static magnetic field and the vein 842 perpendicular to the direction 100 of a static magnetic field on the magnetic susceptibility-weighted images 801 and 821, respectively, are compared.

As a result, it can be seen that contrast difference with respect to surrounding tissues is not emphasized so much for most of the veins approximately perpendicular to the direction 100 of the static magnetic field in the magnetic susceptibility-weighted image 801 obtained by the SWI method as shown in the schematic diagram 802, but contrast difference with respect to surrounding tissues is definitely emphasized in the magnetic susceptibility-weighted image 821 obtained according to this embodiment as shown in the schematic diagram 822.

By comparison of the luminance profile 811 and the luminance profile 831, it can be similarly seen that difference of the luminance 812 of the vein 841 and that of the surrounding tissues is small in the magnetic susceptibility-weighted image 801, but difference of the luminance 832 of the vein 841 and that of the surrounding tissues is large in the image 821. This result indicates that the magnetic susceptibility-weighted image obtained by the SWI method suffers from the $B_0$ direction dependency, in which most of veins approximately perpendicular to the $B_0$ direction cannot be emphasized, but the magnetic susceptibility-weighted image obtained according to this embodiment does not suffer from such $B_0$ direction dependency, in which veins of any direction can be emphasized.

As described above, a magnetic susceptibility-weighted image not depending on the $B_0$ direction can be created according to this embodiment. As a result, a magnetic susceptibility-weighted image in which contrast difference of a tissue for which emphasis is desired (for example, vein) and surrounding tissues is emphasized can be created regardless of the type of the MRI apparatus and the direction of the imaging slice.

Further, this embodiment utilizes the difference in the magnetic susceptibility values of tissues for emphasizing the contrast difference. Therefore, a magnetic susceptibility-weighted image in which contrast differences of three or more kinds of tissues are emphasized can also be created. For example, a magnetic susceptibility-weighted image in which contrast differences of the white matter, gray matter, and cerebrospinal fluid are emphasized can be created. By the SWI method, contrast difference of the white matter and the gray matter may scarcely be obtained depending on the direction of the boundary of these two kinds of tissues. However, in the image conversion processing according to this embodiment, magnetic susceptibility weight functions are determined for the white matter, the gray matter, and the cerebrospinal fluid by utilizing different threshold values for magnetic susceptibility values corresponding to the tissues on the basis of the fact that these tissues show different magnetic susceptibility ranges, and a magnetic susceptibility weighting image is obtained by using them. By carrying out the multiplication of this magnetic susceptibility weighting image and an absolute image, a magnetic susceptibility-weighted image in which contrast differences of these three kinds of tissues are emphasized can be created. In addition, the tissue to be emphasized according to this embodiment is not limited to vein, white matter, gray matter, and cerebrospinal fluid.

Second Embodiment

Hereafter, the second embodiment of the present invention will be explained. According to the first embodiment, a magnetic susceptibility-weighted image in which a tissue desired to be emphasized is emphasized is created regardless of the positional relationship of the $B_0$ direction and the imaging slice. On the other hand, according to this embodiment, a magnetic susceptibility-weighted image equivalent to a magnetic susceptibility-weighted image obtained according to the SWI method with an MRI apparatus of an arbitrary direction of the magnetic field regardless of the positional relationship of the $B_0$ direction and the imaging slice.

The MRI apparatus according to this embodiment has basically the same configurations as those of the first embodiment. Further, the functions realized by the computer 209 according to this embodiment are also basically the same as those according to the first embodiment. However, since the methods for creating a magnetic susceptibility-weighted image of the first embodiment and this embodiment are different from each other, the functions and configurations of the image conversion part 322 in the operation part 320 according to this embodiment and the first embodiment are different from each other. The configurations of this embodiment different from those of the first embodiment will be mainly explained below. Also in this embodiment, the functions of the computer 209 are realized by CPU of the computer 209 by loading programs stored in the storage device 211 on a memory, and executing them.

This embodiment will be explained by exemplifying a case where a magnetic susceptibility-weighted image of a contrast equivalent to that of a magnetic susceptibility-weighted image obtained according to the SWI method with the horizontal magnetic field MRI apparatus 102 is obtained by using the vertical magnetic field MRI apparatus 101 as the MRI apparatus. Also in this embodiment, there is used a coordinate system in which the $B_0$ direction is defined to be z direction, among two directions perpendicular to the z direction, the direction perpendicular to the body axis of the subject is defined to be x direction, and the direction parallel to the body axis of the subject to be y direction.

Figure 17:
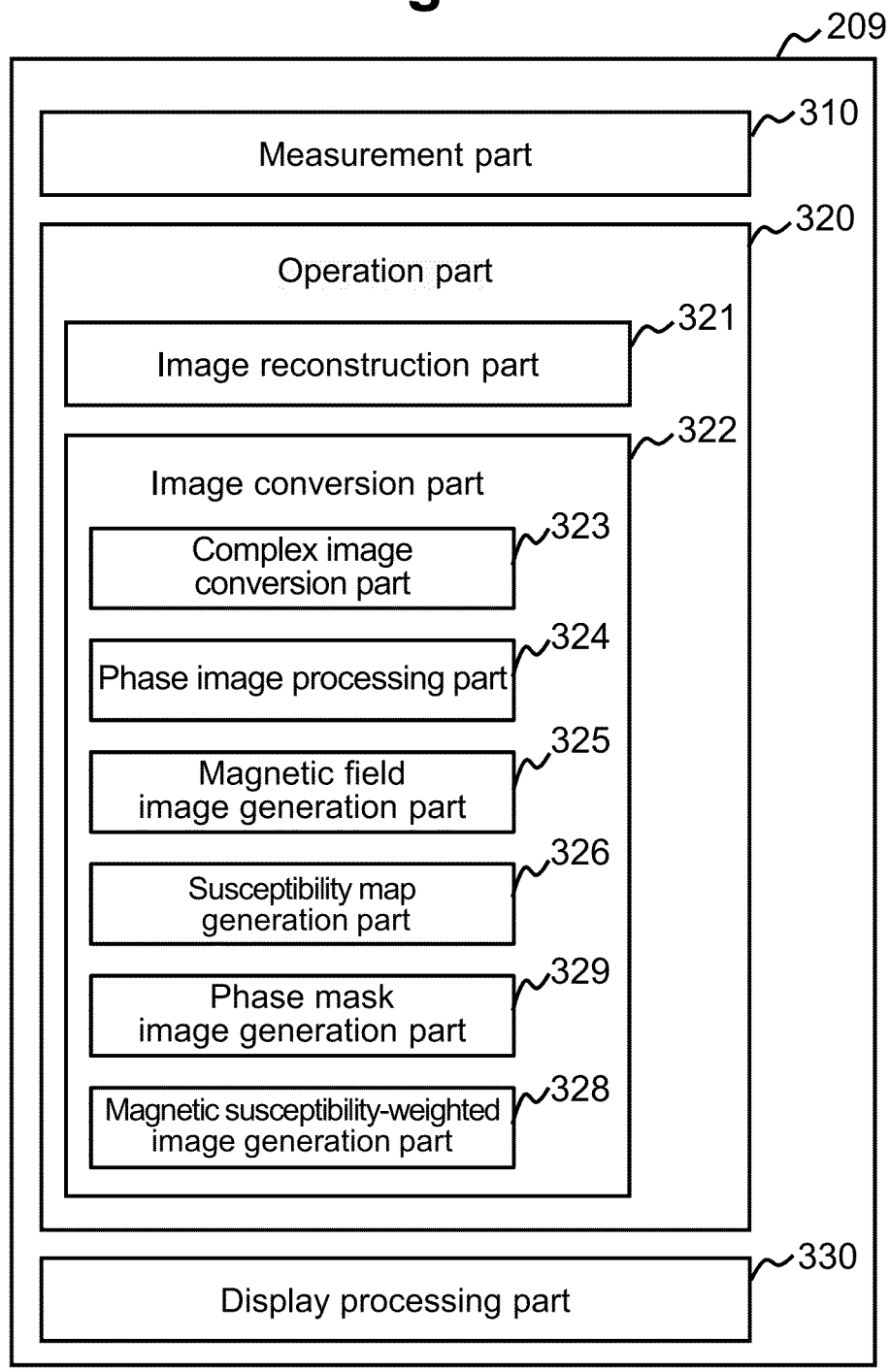
FIG. 17 is a functional block diagram of a computer according to the second embodiment.

As shown in FIG. 17, the image conversion part 322 according to this embodiment is provided with the complex image conversion part 323, the phase image processing part 324, the magnetic field image generation part 325, and the susceptibility map generation part 326, as in the first embodiment. The functions of these parts are the same as those according to the first embodiment. Further, the image conversion part 322 according to this embodiment is provided with a phase mask image generation part 329 instead of the magnetic susceptibility weighting image generation part 327, and the magnetic susceptibility-weighted image generation part 328 generates a magnetic susceptibility-weighted image by using a phase mask image instead of the magnetic susceptibility weighting image. Also in this embodiment, the phase image processing part 324 may not be provided.

The phase mask image generation part 329 creates a phase mask image as a weighting image from a susceptibility map. The phase mask image according to this embodiment is a mask image in which signal intensities of a region of negative phase are reduced for a desired angle between the $B_0$ direction and the imaging slice. According to this embodiment, contrast equivalent to that of a magnetic susceptibility-weighted image obtained with the horizontal magnetic field MRI apparatus 102 is obtained by using the vertical magnetic field MRI apparatus 101 as described above. For this purpose, a mask image is created for a $B_0$ direction different from the actual $B_0$ direction by 90 degrees.

Figure 18:
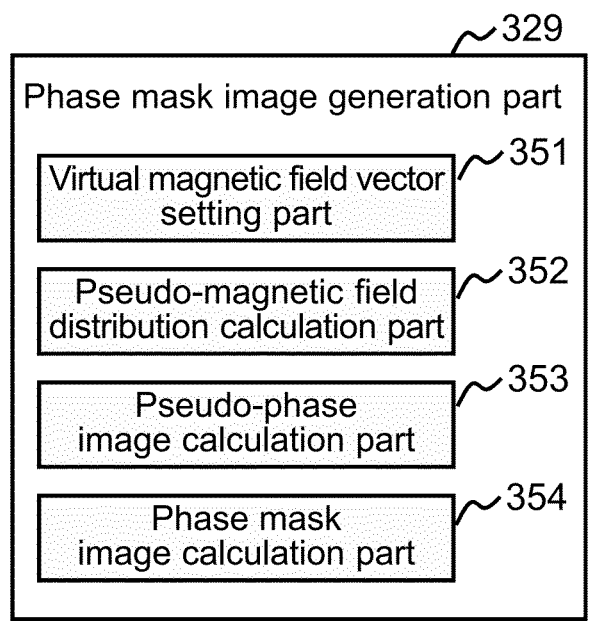
FIG. 18 is a functional block diagram of the phase mask image generation part according to the second embodiment.

In order to realize the above, the phase mask image generation part 329 according to this embodiment is provided with a virtual magnetic field vector setting part 351, a pseudo-magnetic field distribution calculation part 352, a pseudo-phase image calculation part 353, and a phase mask image calculation part 354, as shown in FIG. 18.

The virtual magnetic field vector setting part 351 sets a vector of a $B_0$ direction supposed at the time of creating the mask image (direction of virtual magnetic field), which is different from the actual $B_0$ direction (virtual magnetic field direction vector). According to this embodiment, the direction of the magnetic field in the horizontal magnetic field MRI apparatus 102, i.e., the y direction, is regarded as the direction of the virtual magnetic field direction.

The pseudo-magnetic field distribution calculation part 352 calculates a pseudo magnetic field distribution to be generated when a static magnetic field of the virtual magnetic field direction vector is virtually applied as a pseudo-magnetic field distribution from the susceptibility map and the virtual magnetic field direction vector. The pseudo-magnetic field distribution is calculated by using the equation (15) representing relationship between magnetic field and magnetic susceptibility.

[Equation 15]

$$\delta(r) = \frac{1}{4\pi} \int \chi(r') \frac{3\cos^2\alpha - 1}{|r' - r|^3} d^3 r' \quad (15)$$

In the equation, $\delta(r)$ represents pseudo-magnetic field intensity at a position r in an image, $\chi(r)$ represents magnetic susceptibility at the position r in the image, and $\alpha$ represent angle between the direction of the virtual magnetic field direction vector (y direction) and the vector (r'−r). Further, $\cos\alpha$ is represented by the following equations (16).

[Equation 16]

$$\cos\alpha = \frac{|r'_y - r_y|}{|r' - r|} \quad (16)$$

$r'_y$ and $r_y$ are y components of the vectors r and r', respectively. Further, the method for calculating the pseudo-magnetic field distribution is not limited to the aforementioned method. For example, the pseudo-magnetic field distribution may be calculated by multiplying the susceptibility map with a constant of an appropriate value.

The pseudo-phase image calculation part 353 generates a pseudo-phase image from the obtained pseudo-magnetic field distribution in accordance with the equation (17).

[Equation 17]

$$\phi(r) = -\frac{\delta(r)}{\gamma B_0 \tau_{TE}} \quad (17)$$

$\phi(r)$ represents phase at the position r, and $\gamma$ represents magnetic rotation ratio. $\gamma$ of proton as the object of imaging by MRI is $267.4 \times 10^6$ T$^{-1}$s$^{-1}$. Further, the values of the constants $\tau_{TE}$ and $B_0$ in the equation (17) can be arbitrarily decided.

The phase mask image calculation part 354 calculates a phase mask image using a known method such as the method described in Patent document 1. For example, a phase mask image is created by conversion into a phase image in which the value range of declination of pixels is [−Π, Π], and further conversion of the value range into [0, 1]. According to this embodiment, as the phase image used for the calculation of the phase mask image, the pseudo-phase image calculated by the aforementioned pseudo-phase image calculation part 353 is used. The phase mask image to be calculated is a mask image in which phase difference in the pseudo-phase image is emphasized, as in the conventional SWI method.

In addition, the phase mask image generation part 329 can create a phase mask image for an arbitrary direction of the magnetic field by changing the direction of the virtual static magnetic field applied for obtaining the pseudo-magnetic field distribution. It is most effective to set the direction of the virtual static magnetic field to be the direction perpendicular to the imaging slice.

The magnetic susceptibility-weighted image generation part 328 generates a magnetic susceptibility-weighted image by using the phase mask image as a weighting image for performing weighting for emphasizing contrast difference between a tissue of interest and surrounding tissues, instead of the magnetic susceptibility weighting image. Specifically, the magnetic susceptibility-weighted image is generated by multiplication of the phase mask image generated by the phase mask image generation part 329 and the absolute image for every pixel. The pixel value E(i) of a pixel i in the magnetic susceptibility-weighted image can be calculated in accordance with the equation (18).

[Equation 18]

$$E(i)=P(i) \times S(i) \qquad (18)$$

In the equation, P(i) is pixel value of a pixel i in the phase mask image, and S(i) is pixel value in the absolute image.

The flow of the image conversion processing performed by the image conversion part 322 according to this embodiment will be explained. FIG. 19 shows the process flow of the image conversion processing according to this embodiment.

The complex image conversion part 323 calculates an absolute image and a phase image from a complex image in the same manner as that of the first embodiment (Step S2101). Then, the phase image processing part 324 performs a phase image conversion processing for the phase image in the same manner as that of the first embodiment (Step S2102). Then, the magnetic field image generation part 325 generates a magnetic field image from the phase image in the same manner as that of the first embodiment (Step S2103). Then, the susceptibility map generation part 326 calculates a susceptibility map from the magnetic field image in the same manner as that of the first embodiment (Step S2104). Further, the phase mask image generation part 329 generates a phase mask image in which the phase difference in the pseudo-phase image is emphasized from the susceptibility map by the aforementioned method (Step S2105). Then, the magnetic susceptibility-weighted image generation part 328 generates a magnetic susceptibility-weighted image by multiplication of the phase mask image and the absolute image (Step S2106).

As explained above, the magnetic resonance imaging apparatus 101 according to this embodiment comprises the measurement part 310 for applying a radio frequency magnetic field and a gradient magnetic field to the subject 203 placed in a static magnetic field and detecting magnetic resonance signals generated from the subject 203 as complex signals, the operation part 320 for performing an operation for the complex signals to generate an image, and the display processing part 330 for displaying the generated image on the display device 210, wherein the operation part 320 comprises the image reconstruction part 321 for reconstructing a complex image in which pixel values are complex numbers from the complex signals, and the image conversion part 322 for converting the complex image into a magnetic susceptibility-weighted image, and the image conversion part 322 comprises the complex image conversion part 323 for generating an absolute image and a phase image from absolute value components and phase components of the complex numbers of pixels of the complex image, respectively, the magnetic field image generation part 325 for generating a magnetic field image representing spatial distribution of magnetic field intensity from the phase image, the susceptibility map generation part 326 for generating a susceptibility map from the magnetic field image, the weighting image generation part (phase mask image generation part 329) for generating a weighting image for performing weighting for emphasizing contrast difference of a tissue of interest and surrounding tissues from the susceptibility map, and the magnetic susceptibility-weighted image generation part 328 for generating a magnetic susceptibility-weighted image by multiplication of the absolute image and the weighting image.

The weighting image is a phase mask image in which signal intensities of a region of negative phase are reduced for a desired angle between the $B_0$ direction and the imaging slice, and the weighting image generation part (phase mask image generation part 329) comprises the virtual magnetic field vector setting part 351 for setting a vector of a direction different from the $B_0$ direction as a virtual magnetic field direction vector, the pseudo-magnetic field distribution calculation part 352 for calculating a pseudo-magnetic field distribution to be generated when a static magnetic field of the virtual magnetic field direction vector is virtually applied from the susceptibility map and the virtual magnetic field direction vector, the pseudo-phase image calculation part 353 for calculating a pseudo-phase image from the pseudo-magnetic field distribution, and the phase mask image calculation part 354 for calculating a phase mask image in which phase difference is emphasized on the basis of luminance values of the pseudo-phase image.

That is, according to this embodiment, a magnetic susceptibility-weighted image of contrast equivalent to that of a magnetic susceptibility-weighted image obtained by the SWI method with an MRI apparatus of a $B_0$ direction different from that of the MRI apparatus used for the imaging can be created. For example, a magnetic susceptibility-weighted image of contrast equivalent to that of a magnetic susceptibility-weighted image obtained by the SWI method with a horizontal magnetic field MRI apparatus can be created by using a vertical magnetic field MRI apparatus. Therefore, for example, comparison of images obtained with different MRI apparatuses is enabled.

In the above explanation of this embodiment, a phase mask image in which phase contrast is emphasized is calculated from a pseudo-phase image equivalent to that of a desired $B_0$ direction, and then a magnetic susceptibility-weighted image is calculated by multiplication of the phase mask image and an absolute image. However, the method for the calculation of a magnetic susceptibility-weighted image is not limited to such a method. For example, the pixel values of the pixels (complex numbers) obtained from a pseudo-phase image and an absolute image may be converted by a complex operation in which at least one of rotation and projection on a complex plane is performed, and the converted pixel values may be used as the pixel values of the magnetic susceptibility-weighted image.

Further, although this embodiment is explained above by exemplifying use of the vertical magnetic field MRI apparatus 101, the MRI apparatus to be used is not limited to the vertical magnetic field MRI apparatus 101. The horizontal magnetic field MRI apparatus 102, or an MRI apparatus having a magnet of another shape may also be used.

Further, the aforementioned embodiments are explained by exemplifying the case where the functions of the image reconstruction part, the image conversion part, and the display processing part are realized within the computer provided in the MRI apparatus, but the present invention is not limited to such a configuration. For example, at least one of those parts may be constructed in an information processor independent from the MRI apparatus and able to transmit and receive data to and from the computer 209 of the MRI apparatus.

DENOTATION OF REFERENCE NUMERALS

100: Direction of static magnetic field, 101: vertical magnetic field MRI apparatus, 102: horizontal magnetic field MRI apparatus, 103: MRI apparatus, 201: magnet, 202: gradient coil, 203: subject, 204: sequencer, 205: gradient magnetic field power supply, 206: radio frequency magnetic field generator, 207: probe, 208: receiver, 209: computer, 210: display device, 211: storage device, 310: measurement part, 320: operation part, 321: image reconstruction part, 322: image conversion part, 323: complex image conversion part, 324: phase image processing part, 325: magnetic field image generation part, 326: susceptibility map generation part, 327: magnetic susceptibility weighting image generation part, 328: magnetic susceptibility-weighted image generation part, 329: phase mask image generation part, 330: display processing part, 341: threshold value determination part, 342: weighting image calculation part, 351: virtual magnetic field vector setting part, 352: pseudo-magnetic field distribution calculation part, 353: pseudo-phase image calculation part, 354: phase mask image calculation part, 361: phase threshold value calculation part, 362: phase histogram calculation part, 363: magnetic susceptibility histogram calculation part, 364: histogram standard deviation calculation part, 365: magnetic susceptibility threshold value calculation part, 401: slice gradient magnetic field pulse, 402: RF pulse, 403: slice encoding gradient magnetic field pulse, 404: phase encoding gradient magnetic field pulse, 406: read-out gradient magnetic field pulse, 407: echo, 408: slice encoding gradient magnetic field pulse, 409: phase encoding gradient magnetic field pulse, 501: phase image, 502: phase image, 503: phase image, 511: luminance profile, 512: luminance profile, 513: luminance profile, 521: phase image, 522: phase image, 523: phase image, 531: luminance profile, 532: luminance profile, 533: luminance profile, 541: vein, 542: vein, 543: vein, 601: magnetic susceptibility-weighted image obtained by SWI method, 602: magnetic susceptibility-weighted image obtained by SWI method, 603: magnetic susceptibility-weighted image obtained by SWI method, 611: luminance profile, 612: luminance profile, 613: luminance profile, 621: magnetic susceptibility-weighted image obtained according to this embodiment, 622: magnetic susceptibility-weighted image obtained according to this embodiment, 623: magnetic susceptibility-weighted image obtained according to this embodiment, 631: luminance profile, 632: luminance profile, 633: luminance profile, 701: phase image, 711: vein, 712: vein, 721: schematic diagram, 722: schematic diagram, 731: luminance profile, 732: luminance profile, 741: luminance, 742: luminance, 801: magnetic susceptibility-weighted image obtained by SWI method, 802: schematic diagram, 811: luminance profile, 812: luminance, 821: magnetic susceptibility-weighted image obtained according to this embodiment, 822: schematic diagram, 831: luminance profile, 832: luminance, 841: vein, 842: vein

The invention claimed is:

1. A magnetic resonance imaging apparatus comprising a measurement part for applying a radio frequency magnetic field and a gradient magnetic field to a subject placed in a static magnetic field and detecting magnetic resonance signals generated from the subject as complex signals, an operation part for performing an operation for the complex signals to generate an image, and a display processing part for displaying the generated image on a display device, wherein:

the operation part comprises:
an image reconstruction part for reconstructing a complex image in which pixel values are complex numbers from the complex signals, and
an image conversion part for converting the complex image into a magnetic susceptibility-weighted image, and
the image conversion part comprises:
a complex image conversion part for generating an absolute image and a phase image from absolute value components and phase components of the complex numbers of pixels of the complex image, respectively,
a magnetic field image generation part for generating a magnetic field image representing spatial distribution of magnetic field intensity from the phase image,
a susceptibility map generation part for generating a susceptibility map from the magnetic field image,
a weighting image generation part for generating a weighting image for performing weighting for emphasizing contrast difference of a tissue of interest and a surrounding tissue from the susceptibility map, and
a magnetic susceptibility-weighted image generation part for generating a magnetic susceptibility-weighted image by multiplication of the absolute image and the weighting image.

2. The magnetic resonance imaging apparatus according to claim 1, wherein:
the weighting image is a magnetic susceptibility weighting image for emphasizing magnetic susceptibility difference.

3. The magnetic resonance imaging apparatus according to claim 2, wherein:
the weighting image generation part comprises:
a threshold value determination part for determining one or more magnetic susceptibility threshold values on the basis of luminance values of the susceptibility map, and
a weighting image calculation part for calculating the weighting image from the susceptibility map and the magnetic susceptibility threshold value or values determined by the threshold value determination part.

4. The magnetic resonance imaging apparatus according to claim 3, wherein:
the threshold value determination part determines a first magnetic susceptibility threshold value and a second magnetic susceptibility threshold value having a value larger than the first magnetic susceptibility threshold value on the basis of the luminance values of the susceptibility map, and
the weighting image calculation part sets, as for the pixels of the susceptibility map, weights of the pixels having a luminance value smaller than the first magnetic susceptibility threshold value to be a predetermined first weight value, weights of the pixels having a luminance value larger than the second magnetic susceptibility threshold value to be a predetermined second weight value different from the first weight value, and weights of the pixels having a luminance value between the first magnetic susceptibility threshold value and the second magnetic susceptibility threshold value to be a weight value calculated according to a predetermined function connecting the first weight value and the second weight value.

5. The magnetic resonance imaging apparatus according to claim 3, wherein:
the threshold value determination part comprises:
a phase threshold value calculation part for determining one or more phase threshold values from pixel values of the phase image, a phase histogram calculation part for calculating a phase histogram as a histogram of the pixel values of the phase image, a magnetic susceptibility histogram calculation part for calculating a magnetic susceptibility histogram as a histogram of pixel values of the susceptibility map, a histogram standard deviation calculation part for calculating standard deviations of the phase histogram and the magnetic susceptibility histogram, and a magnetic susceptibility threshold value calculation part for calculating one or more of the magnetic susceptibility threshold values by using the phase threshold value or values, the standard deviation of the phase histogram, and the standard deviation of the magnetic susceptibility histogram.

6. The magnetic resonance imaging apparatus according to claim 1, wherein:

the weighting image is a phase mask image in which signal intensities of a negative phase region are reduced for a desired angle between a $B_0$ direction and an imaging slice direction.

7. The magnetic resonance imaging apparatus according to claim 6, wherein:

the weighting image generation part comprises:

a virtual magnetic field vector setting part for setting a vector of a direction different from the $B_0$ direction as a virtual magnetic field direction vector, a pseudo-magnetic field distribution calculation part for calculating a pseudo magnetic field distribution as a pseudo-magnetic field distribution generated when a static magnetic field of the virtual magnetic field direction vector is virtually applied from the susceptibility map and the virtual magnetic field direction vector, a pseudo-phase image calculation part for calculating a pseudo phase image as a pseudo-phase image from the pseudo-magnetic field distribution, and a phase mask image calculation part for calculating a phase mask image in which phase difference is emphasized on the basis of luminance values of the pseudo-phase image.

8. The magnetic resonance imaging apparatus according to claim 1, wherein:

the image conversion part further comprises a phase image processing part for performing image processing for the phase image generated by the complex image conversion part.

9. A magnetic susceptibility-weighted image generation method for generating a magnetic susceptibility-weighted image in which magnetic susceptibility difference is emphasized from a complex image of which pixel values are complex numbers, which comprises:

a complex image conversion step of generating an absolute image and a phase image from absolute value components and phase components of the complex numbers of pixels of the complex image, respectively, a magnetic field image generation step of generating a magnetic field image representing spatial distribution of magnetic field intensity from the phase image, a susceptibility map generation step of generating a susceptibility map from the magnetic field image, a weighting image generation step of generating a weighting image for performing weighting for enhancing contrast difference of a tissue of interest and a surrounding tissue from the susceptibility map, and a magnetic susceptibility-weighted image generation step of generating a magnetic susceptibility-weighted image by multiplication of the absolute image and the weighting image.

\* \* \* \* \*